US010295555B2

(12) United States Patent
Yabutani et al.

(10) Patent No.: US 10,295,555 B2
(45) Date of Patent: May 21, 2019

(54) AUTOMATIC ANALYSIS DEVICE AND ANALYSIS METHOD

(71) Applicant: HITACHI HIGH-TECHNOLOGIES CORPORATION, Tokyo (JP)

(72) Inventors: Chie Yabutani, Tokyo (JP); Akihisa Makino, Tokyo (JP); Shigeki Matsubara, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 51 days.

(21) Appl. No.: 15/032,781

(22) PCT Filed: Dec. 8, 2014

(86) PCT No.: PCT/JP2014/082382
§ 371 (c)(1),
(2) Date: Apr. 28, 2016

(87) PCT Pub. No.: WO2015/098473
PCT Pub. Date: Jul. 2, 2015

(65) Prior Publication Data
US 2016/0274133 A1  Sep. 22, 2016

(30) Foreign Application Priority Data

Dec. 25, 2013 (JP) ................. 2013-267309

(51) Int. Cl.
G01N 33/86 (2006.01)
G01N 35/10 (2006.01)
(Continued)

(52) U.S. Cl.
CPC ....... G01N 33/86 (2013.01); G01N 35/00584 (2013.01); G01N 35/00722 (2013.01);
(Continued)

(58) Field of Classification Search
None
See application file for complete search history.

(56) References Cited

U.S. PATENT DOCUMENTS 4,047,890 A    9/1977  Eichelberger et al.
6,432,657 B1 * 8/2002  Kikuchi ................. G01N 33/86
                                                    435/13
(Continued)

FOREIGN PATENT DOCUMENTS

JP         3036063 B    4/2000
JP    2003-524184 A    8/2003
(Continued)

OTHER PUBLICATIONS

International Preliminary Report on Patentability received in corresponding International Application No. PCT/JP2014/082382 dated Jun. 30, 2016.
(Continued)

Primary Examiner — Benjamin R Whatley
(74) Attorney, Agent, or Firm — Mattingly & Malur, PC

(57) ABSTRACT

A signal reference value (SLocal) is set at which a blood coagulation reaction time (T) of a blood coagulation time reference sample measured on the basis of the result of comparing a signal value (amount of transmitted light, amount of scattered light, amount of fluorescence, or turbidity) pertaining to blood coagulation time that varies temporally according to the mixing and reaction of the blood coagulation time reference sample and a reagent and a signal reference value (S) corresponds to an expected value (Te) for the blood coagulation reaction time that has been set beforehand so as to correspond to the blood coagulation time reference sample. As a result, it is possible to use the blood coagulation time reference sample to determine the state of the reagent and enhance the reliability of measurement results by setting a unique signal reference value for each reagent container.

6 Claims, 20 Drawing Sheets

(51) Int. Cl.
  *G01N 35/00* (2006.01)
  *G01N 35/04* (2006.01)
  *G01N 33/49* (2006.01)

(52) U.S. Cl.
  CPC ..... *G01N 35/1065* (2013.01); *G01N 33/4905* (2013.01); *G01N 35/00693* (2013.01); *G01N 35/00732* (2013.01); *G01N 35/10* (2013.01); *G01N 2035/009* (2013.01); *G01N 2035/0091* (2013.01); *G01N 2035/0097* (2013.01); *G01N 2035/00702* (2013.01); *G01N 2035/00821* (2013.01); *G01N 2035/00891* (2013.01); *G01N 2035/0441* (2013.01); *G01N 2035/0443* (2013.01)

(56) References Cited

U.S. PATENT DOCUMENTS

| | | | |
|---|---|---|---|
| 6,524,861 B1* | 2/2003 | Anderson | G01N 33/86 422/63 |
| 6,752,960 B1* | 6/2004 | Matsubara | G01N 35/1004 422/552 |
| 6,846,457 B1* | 1/2005 | Tokiwa | G01N 35/00594 422/63 |
| 2003/0146113 A1 | 8/2003 | Unkrig et al. | |
| 2008/0158552 A1* | 7/2008 | Tokunaga | G01N 21/253 356/73 |
| 2009/0142231 A1 | 6/2009 | Shibuya et al. | |
| 2010/0235103 A1 | 9/2010 | Carroll et al. | |
| 2011/0014640 A1 | 1/2011 | Yamamoto et al. | |
| 2011/0259129 A1* | 10/2011 | Murata | G01N 35/00693 73/866.3 |
| 2012/0029934 A1 | 2/2012 | Shindo et al. | |
| 2012/0282139 A1 | 11/2012 | Makino et al. | |
| 2012/0315190 A1* | 12/2012 | Adachi | G01N 21/51 422/82.05 |
| 2014/0136123 A1 | 5/2014 | Manri et al. | |
| 2014/0255254 A1* | 9/2014 | Yamaguchi | G01N 33/86 422/73 |

FOREIGN PATENT DOCUMENTS

| | | |
|---|---|---|
| JP | 2005-134259 A | 5/2005 |
| JP | 2009-133796 A | 6/2009 |
| JP | 4799116 B | 10/2011 |
| JP | 2012-026947 A | 2/2012 |
| JP | 2012-242122 A | 12/2012 |
| JP | 2012-252014 A | 12/2012 |
| JP | 5123496 B | 1/2013 |
| WO | 2011/068049 A1 | 9/2011 |

OTHER PUBLICATIONS

International Search Report dated Mar. 10, 2015 and International Preliminary Examination Report dated Dec. 14, 2015.
Extended European Search Report received in corresponding European Application No. 14875287.6 dated Jul. 26, 2017.

* cited by examiner

[FIG. 1]
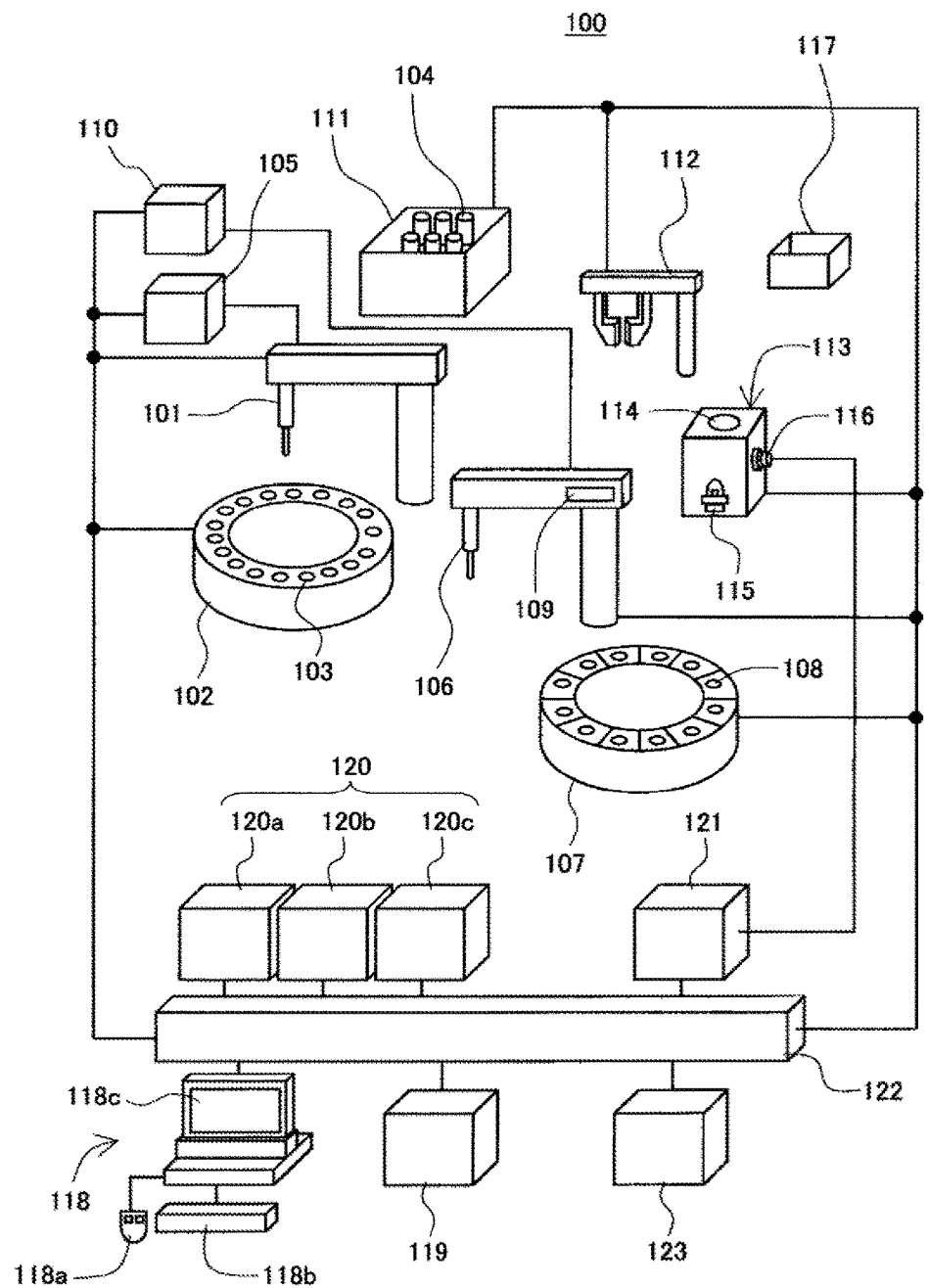

[FIG. 2]
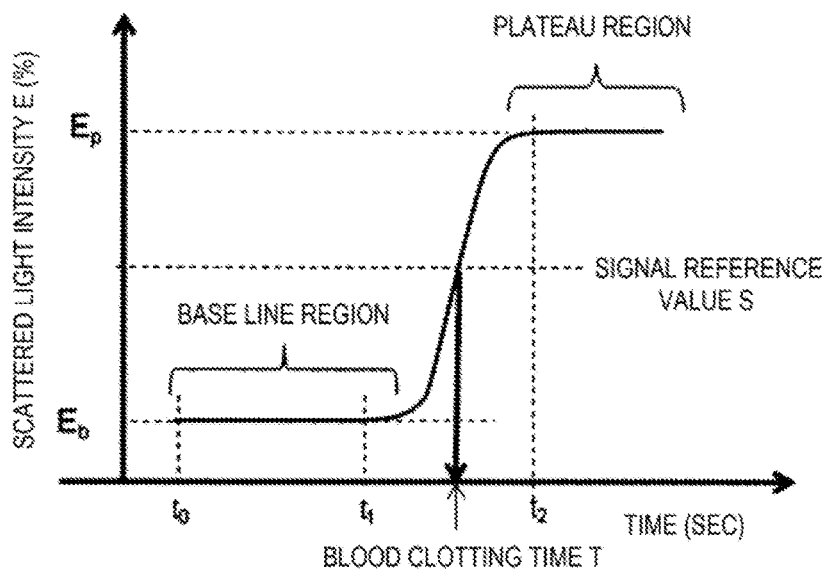
[FIG. 3]
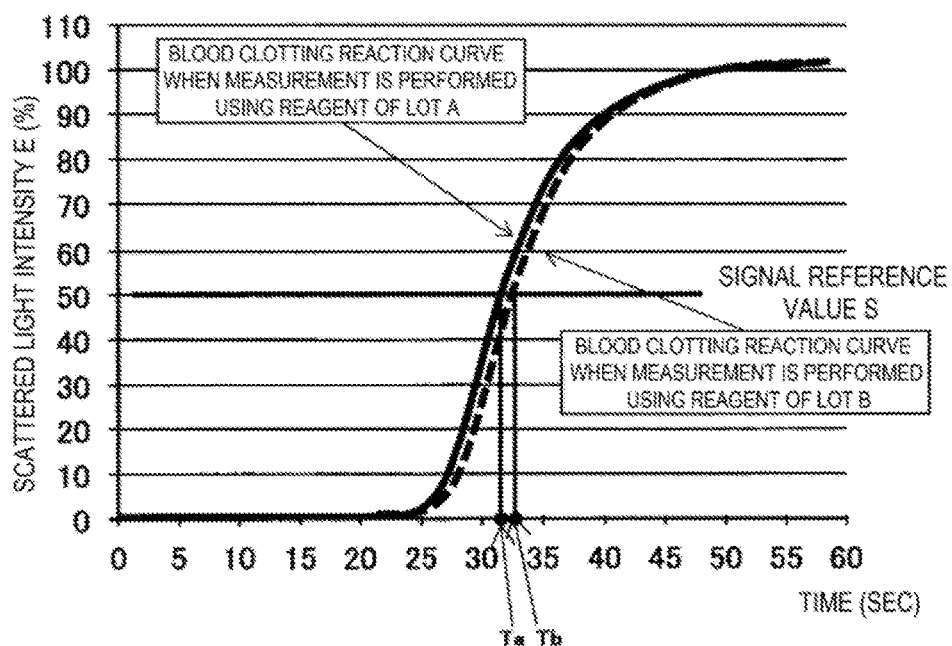

[FIG. 4]
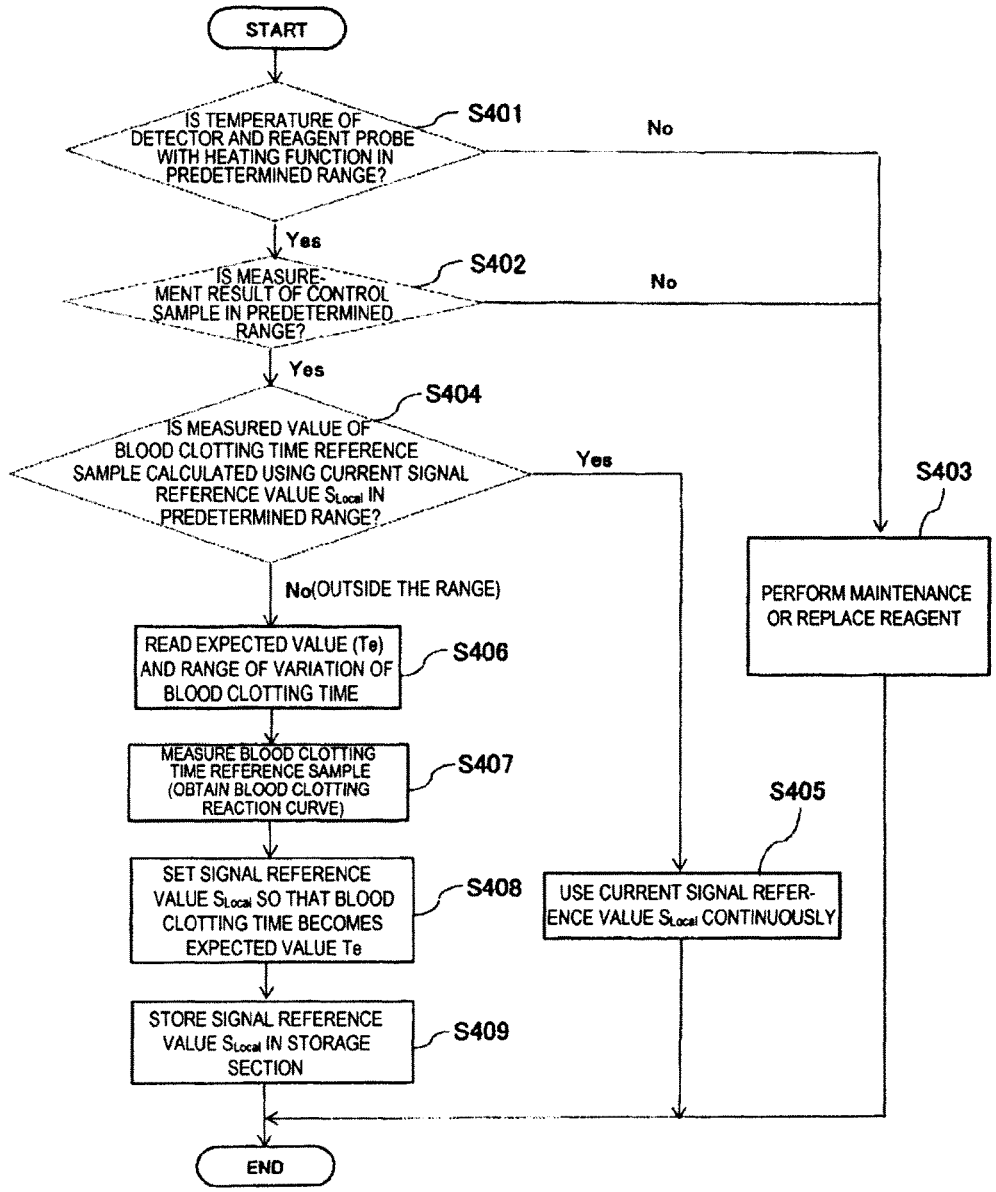

[FIG. 5]
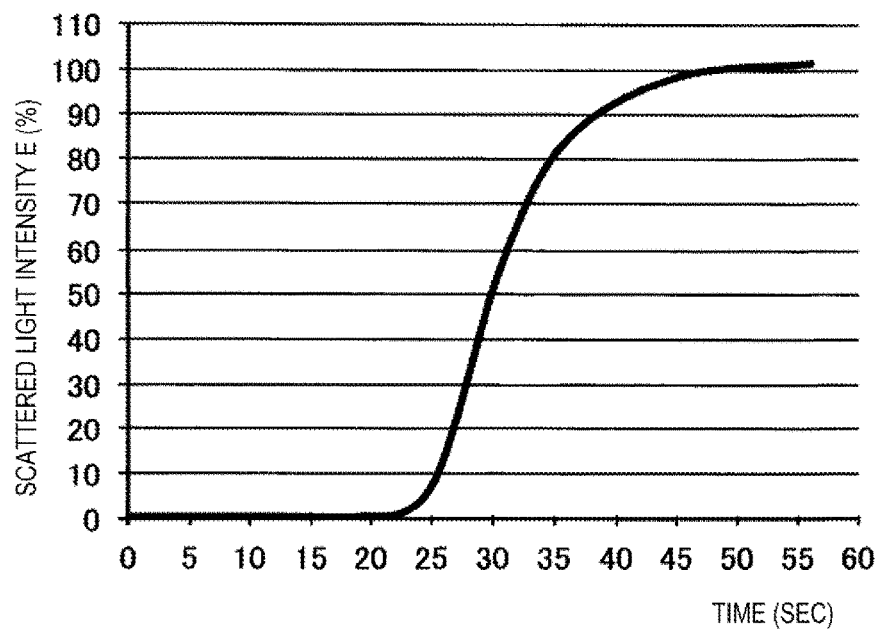
[FIG. 6]
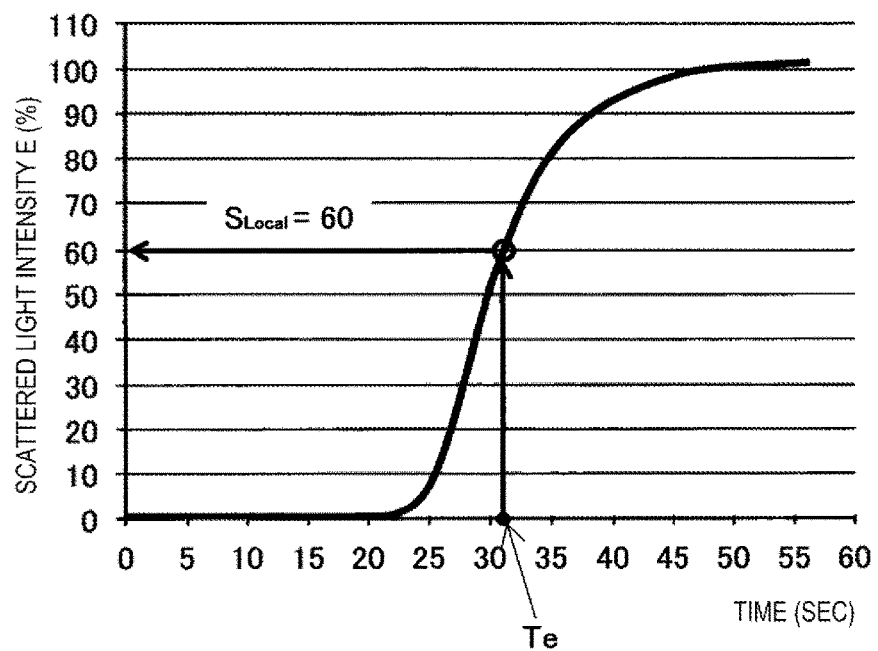

[FIG. 7]
| POSITION | ITEM | LOT | REAGENT VESSEL | SAMPLE | NUMBER OF REMAINING TESTS | THRESHOLD |
|---|---|---|---|---|---|---|
| 1 | APTT | A00001 | 1 | S00001 | 38 | 62% |
| 2 | APTT | A00001 | 2 | S00001 | 200 | 62% |
| 3 | APTT | A00002 | 1 | - | 200 | NOT SET |
| 4 | PT | B00001 | 1 | S00001 | 22 | 50% |
| 5 | PT | B00002 | 1 | S00001 | 200 | 52% |
| 6 | PT | B00002 | 2 | S00001 | 200 | 51% |
| 7 | Fbg | C00001 | 1 | S00001 | 100 | 43% |
| 8 | Fbg | C00001 | 2 | - | 100 | NOT SET |
| 9 | DD | D00001 | 1 | S00002 | 80 | - |
| 10 | AT-III | E0001 | 1 | S00003 | 200 | - |
[FIG. 8]
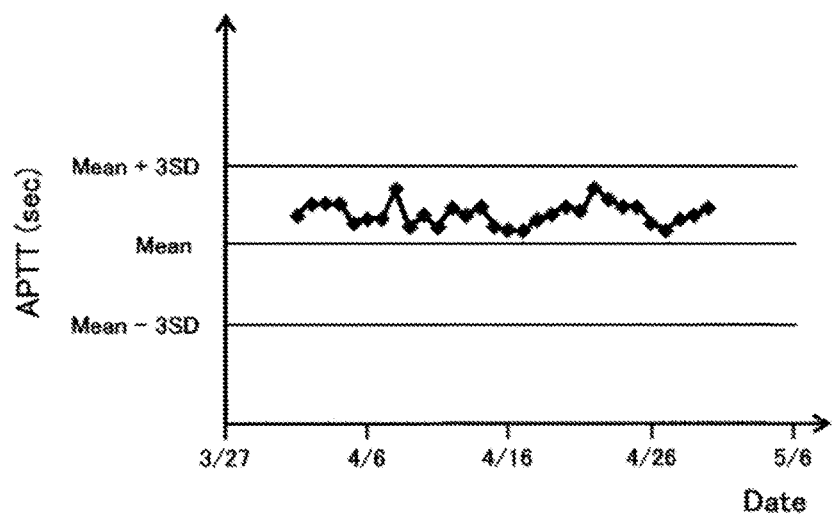

[FIG. 9]
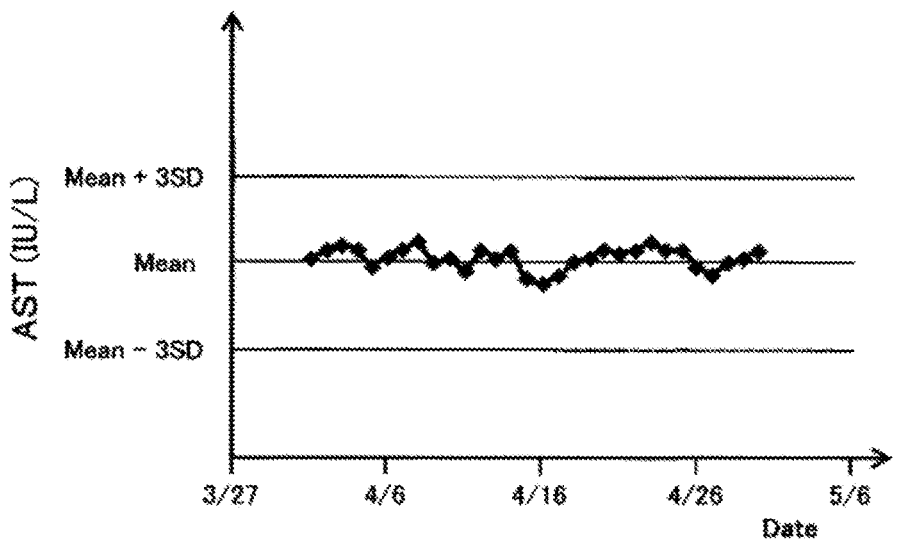
[FIG. 10]
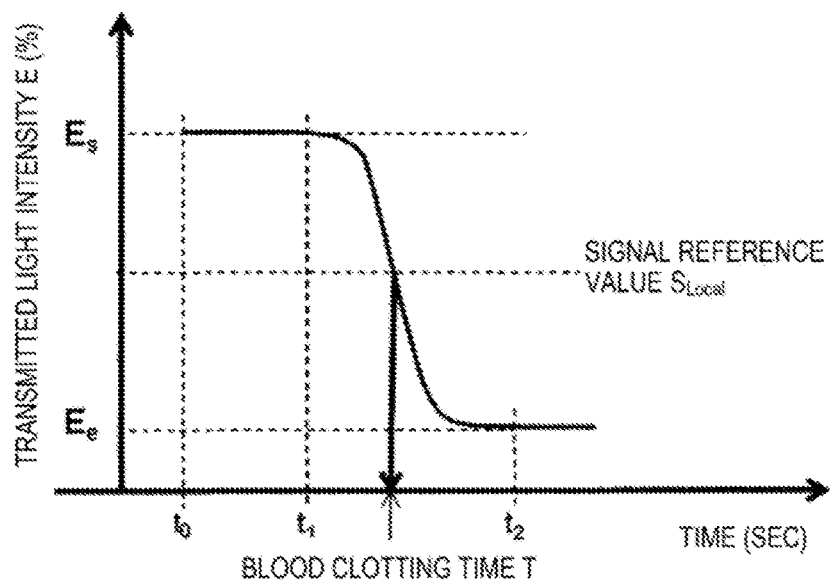

[FIG. 11]
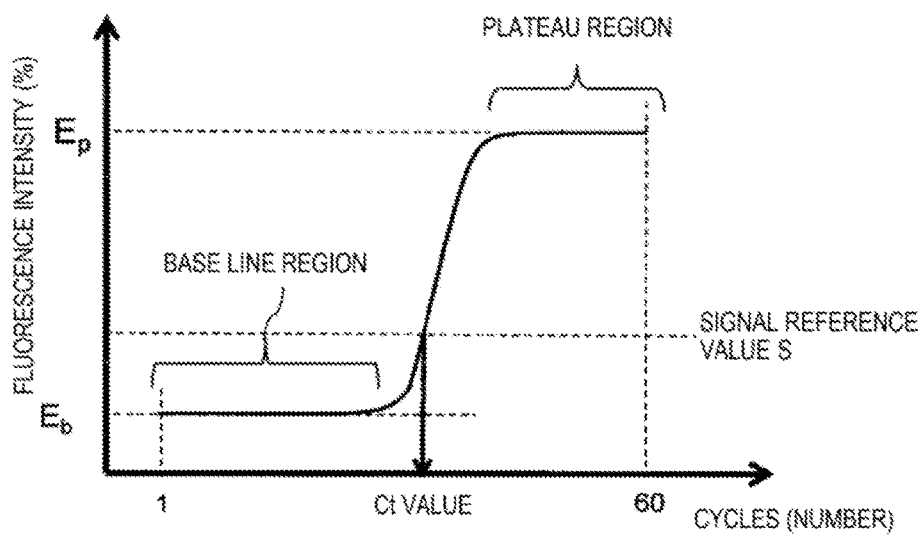
[FIG. 12]
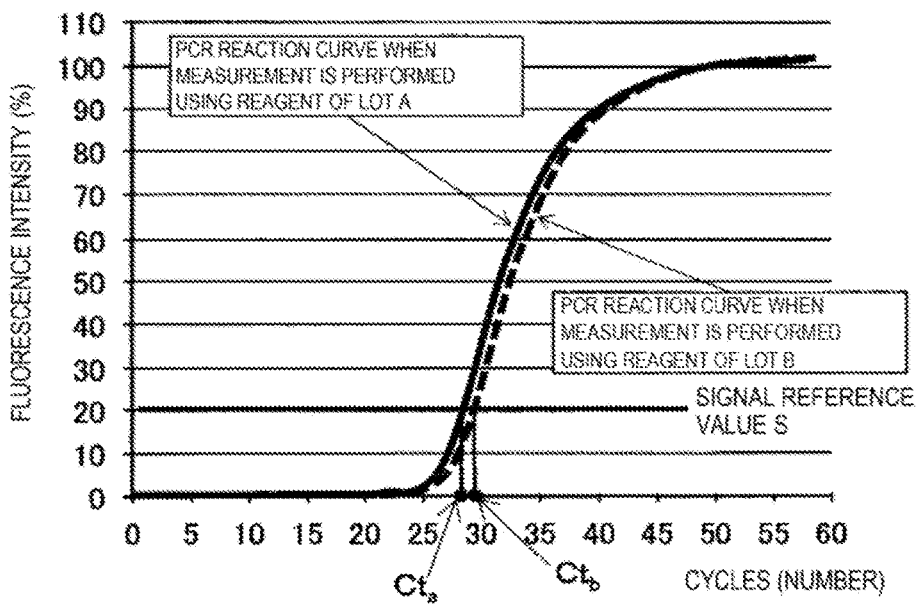

[FIG. 13]
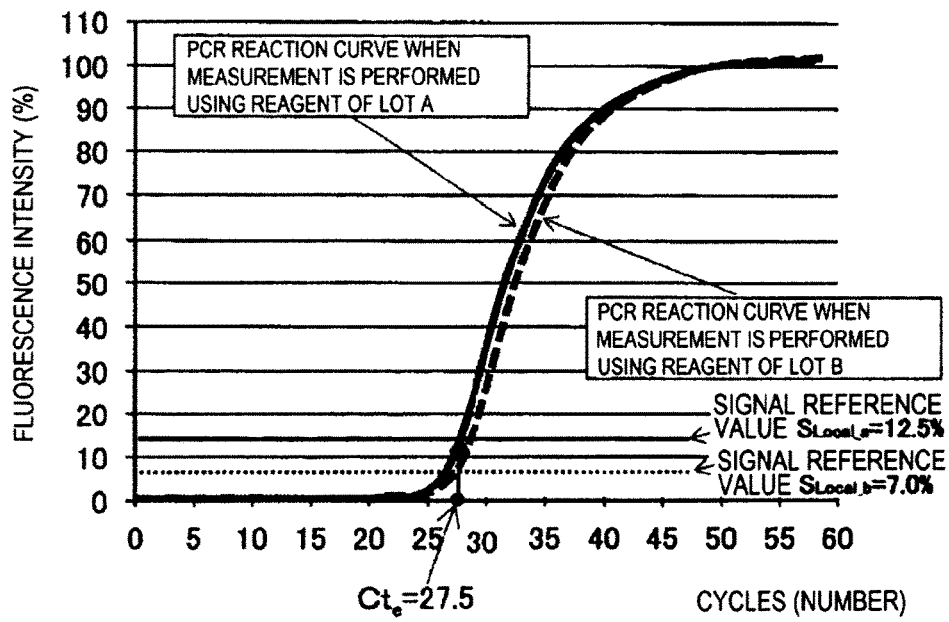
[FIG. 14]
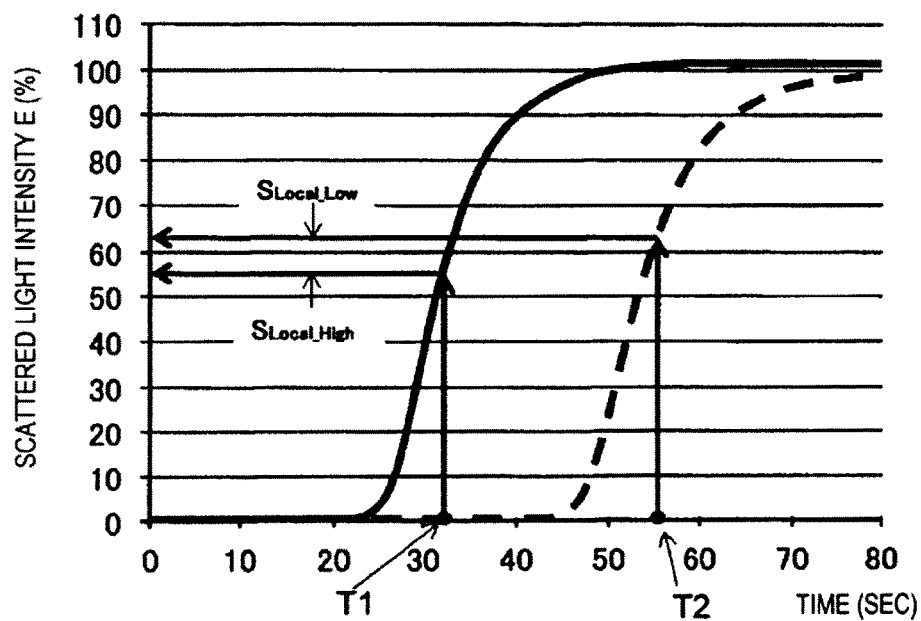

[FIG. 15]
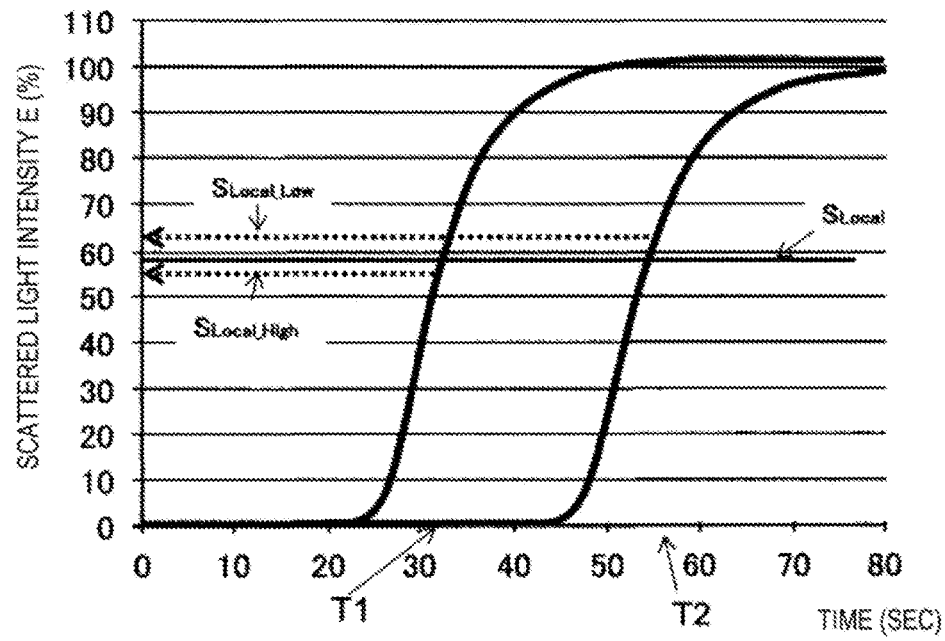
[FIG. 16]
| TYPE OF APPROXIMATE FORMULA | EXAMPLE OF FUNCTION |
|---|---|
| LINEAR APPROXIMATION | $Y = aX + b$ |
| POLYNOMIAL APPROXIMATION | $Y = aX^2 + bX + c$ (QUADRATIC CURVE) |
| LOGARITHMIC APPROXIMATION | $Y = a \cdot Ln(X) + b$ |
| EXPONENTIAL APPROXIMATION | $Y = a \cdot e^{bT}$ |

[FIG. 17A]
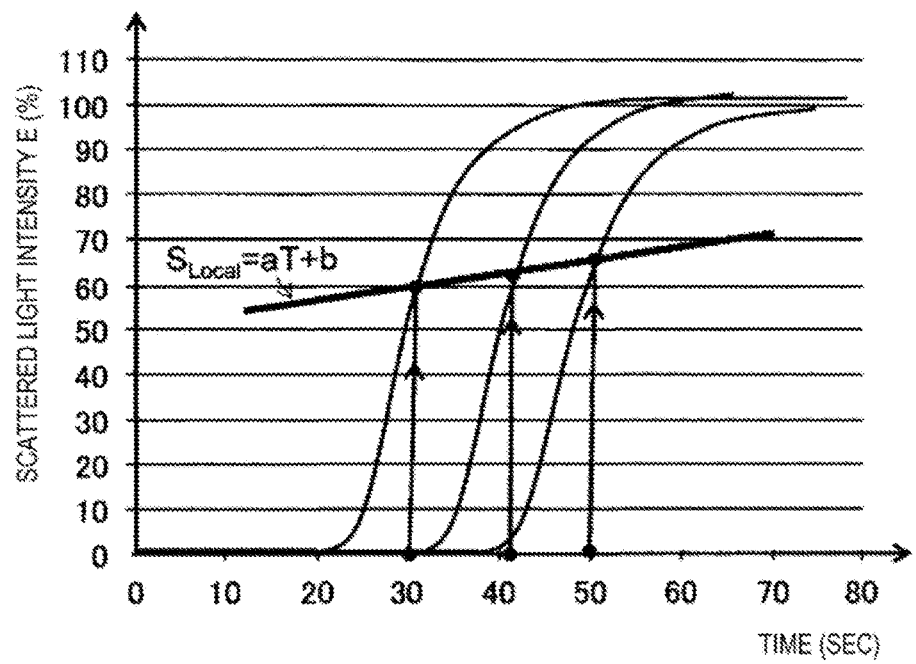
[FIG. 17B]
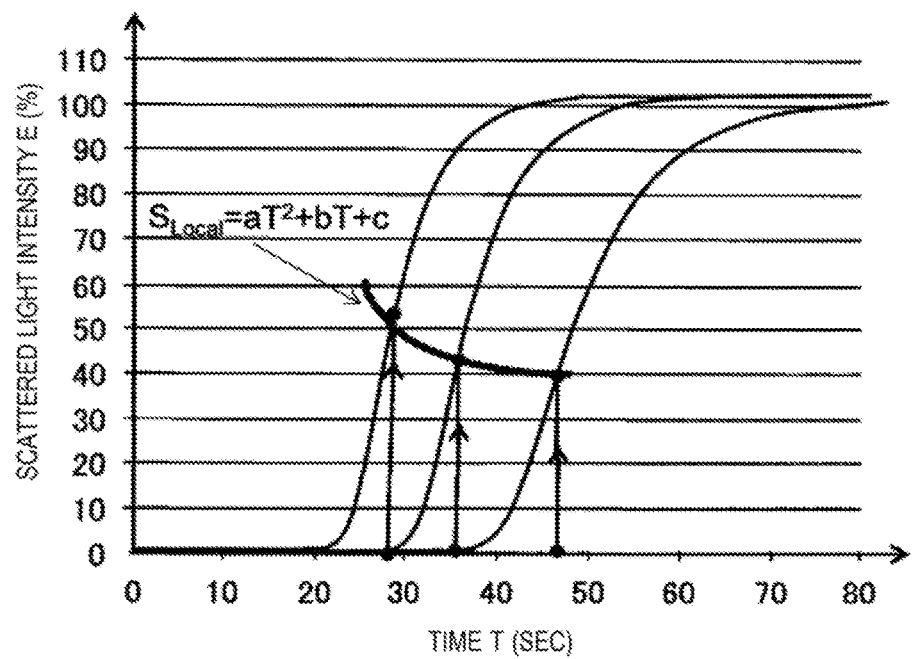

[FIG. 17C]
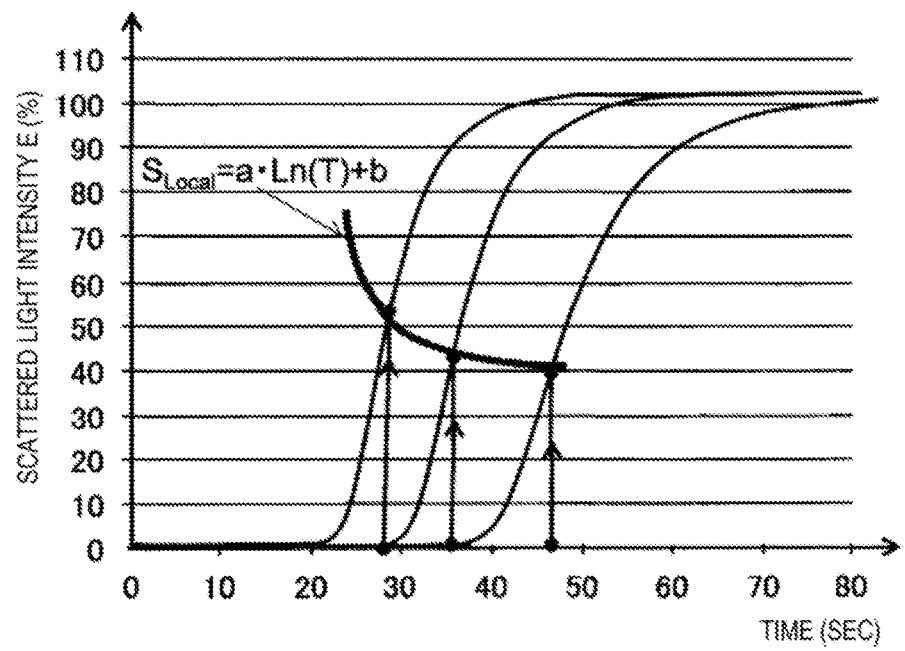
[FIG. 17D]
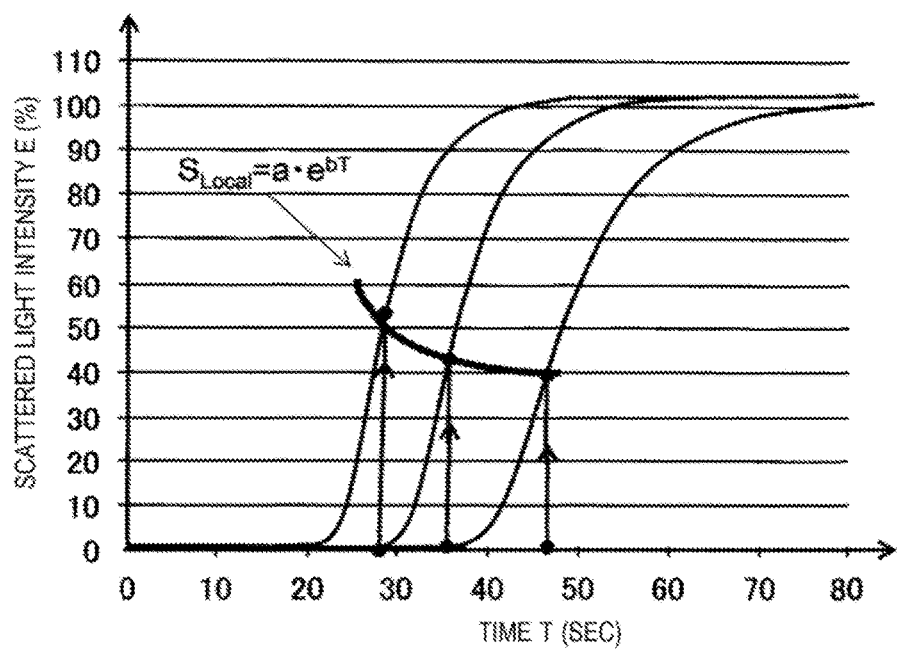

[FIG. 17E]
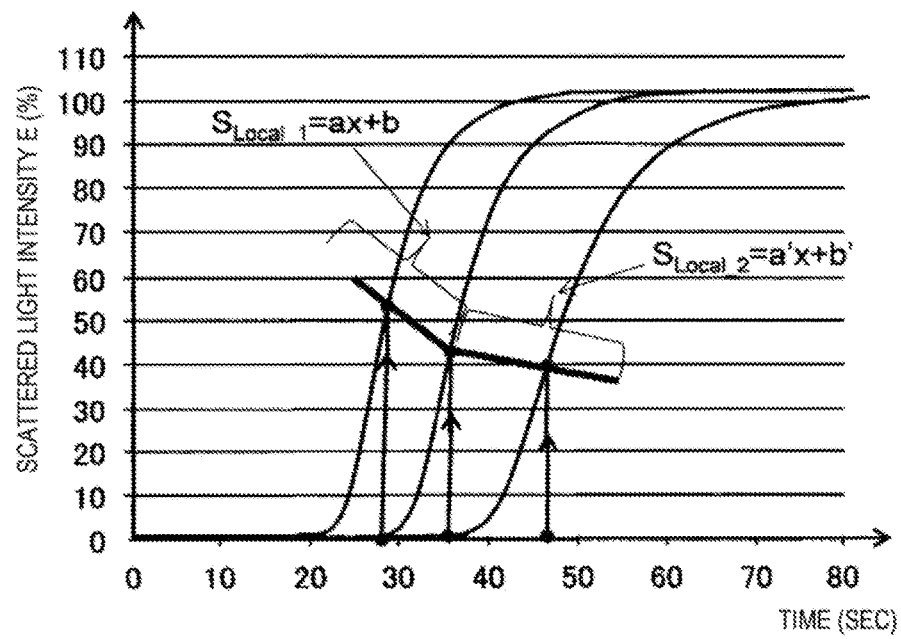
[FIG. 18A]
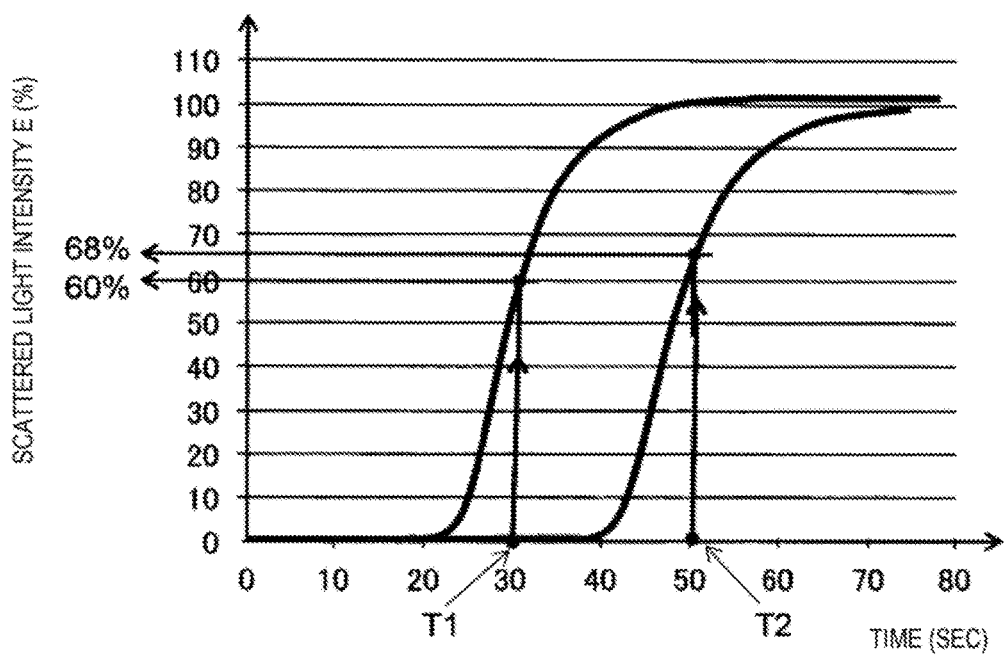

[FIG. 18B]
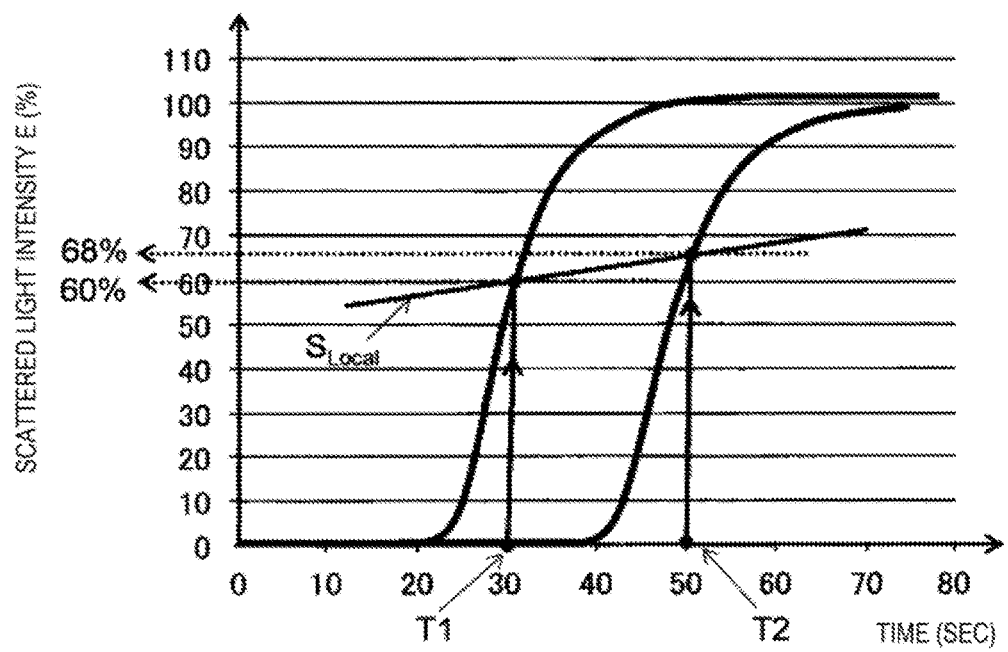
[FIG. 19]
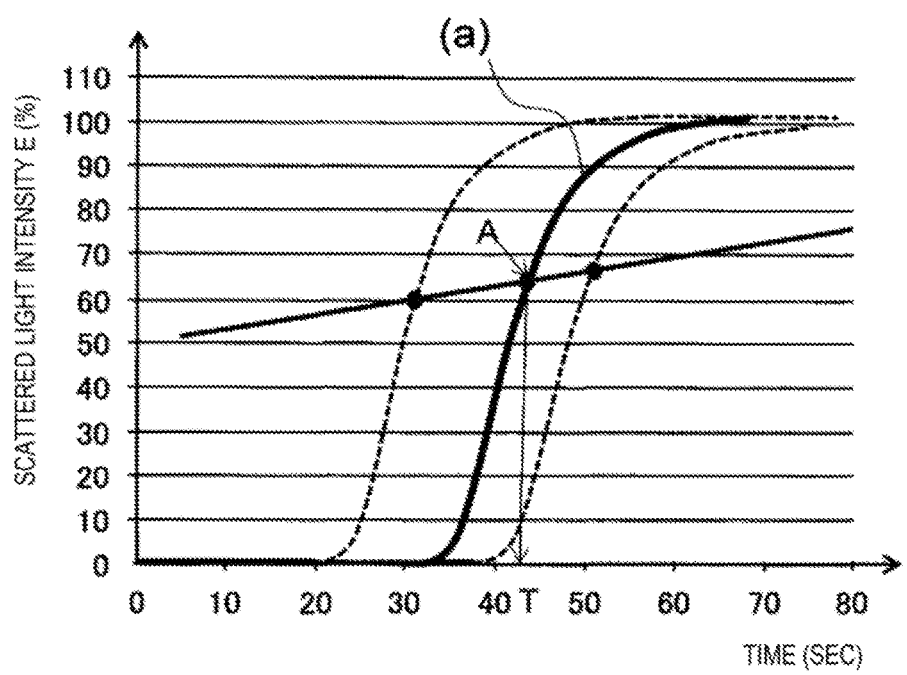

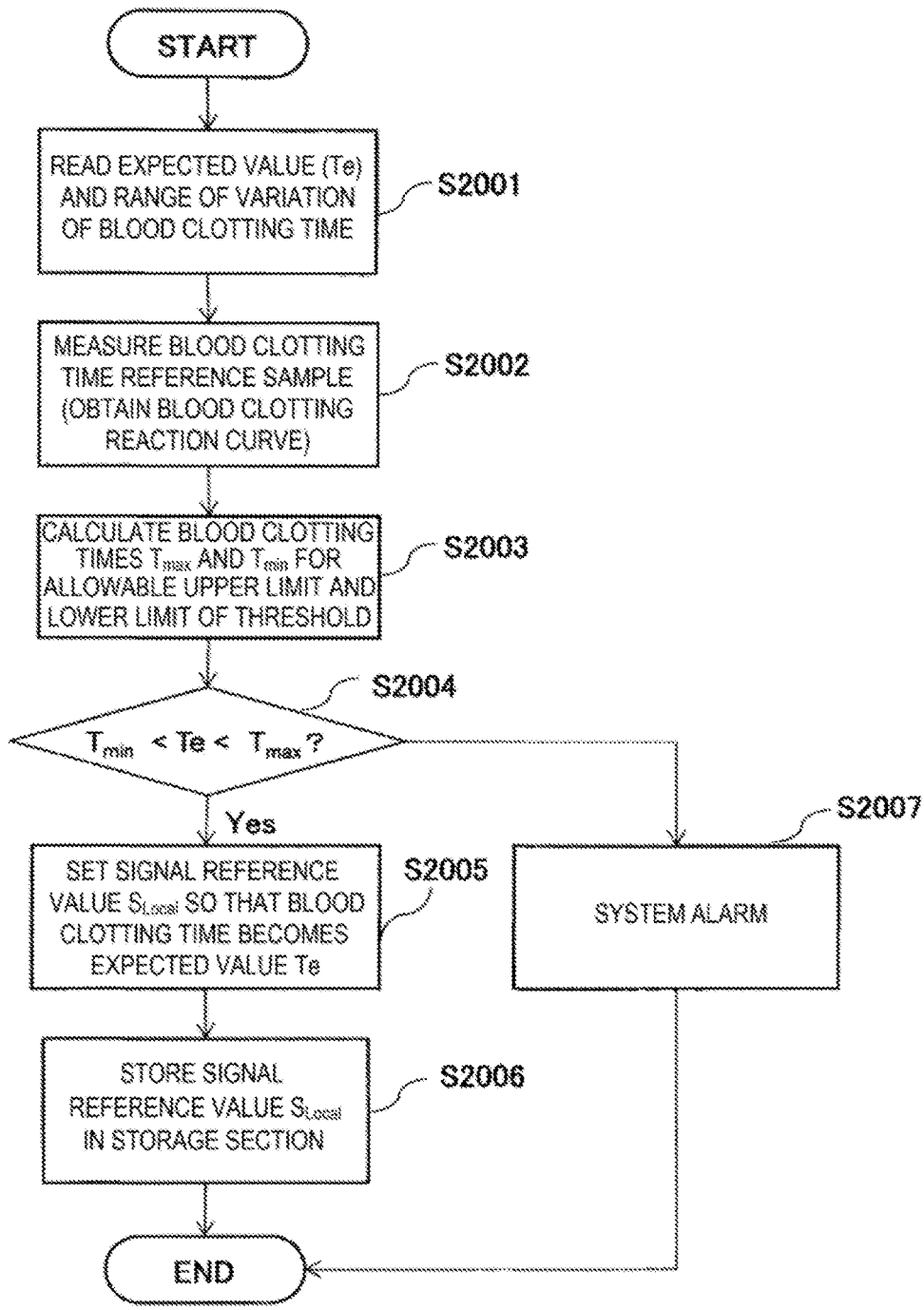
[FIG. 20]

[FIG. 21]
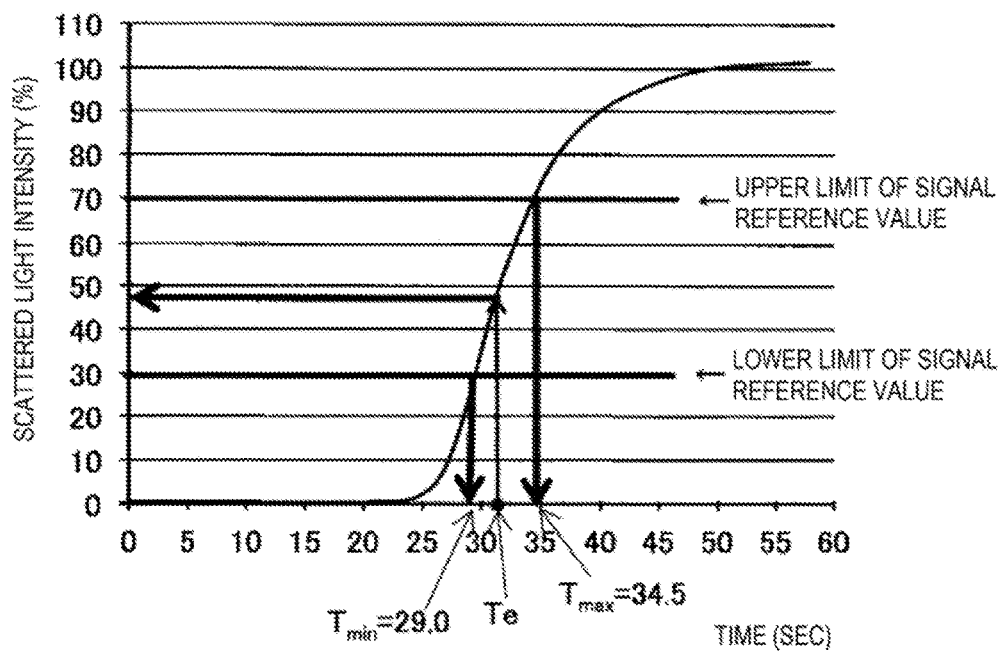
[FIG. 22]
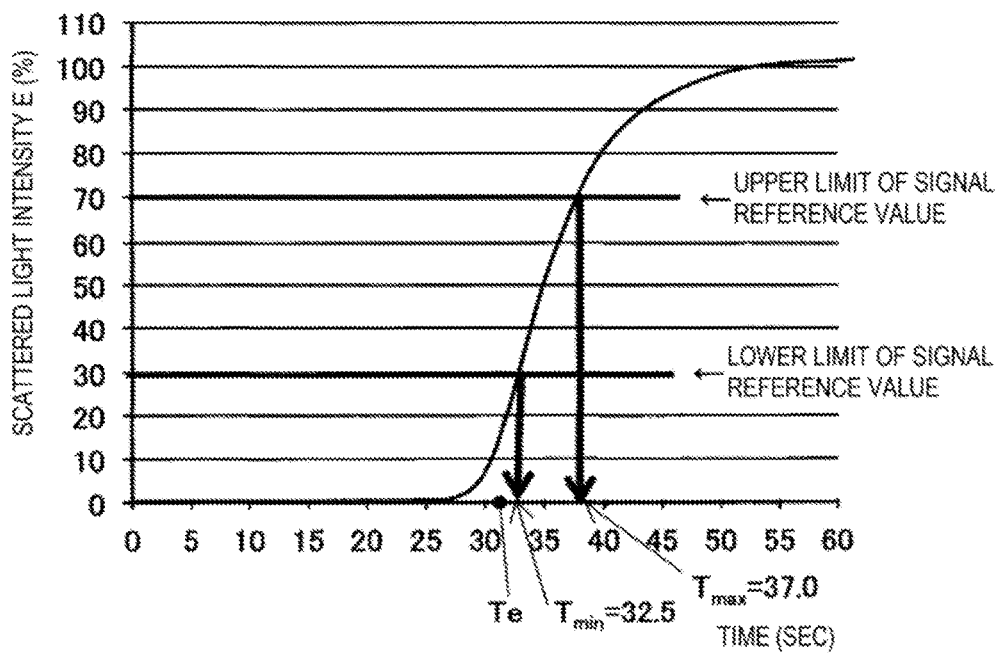

[FIG. 23A]
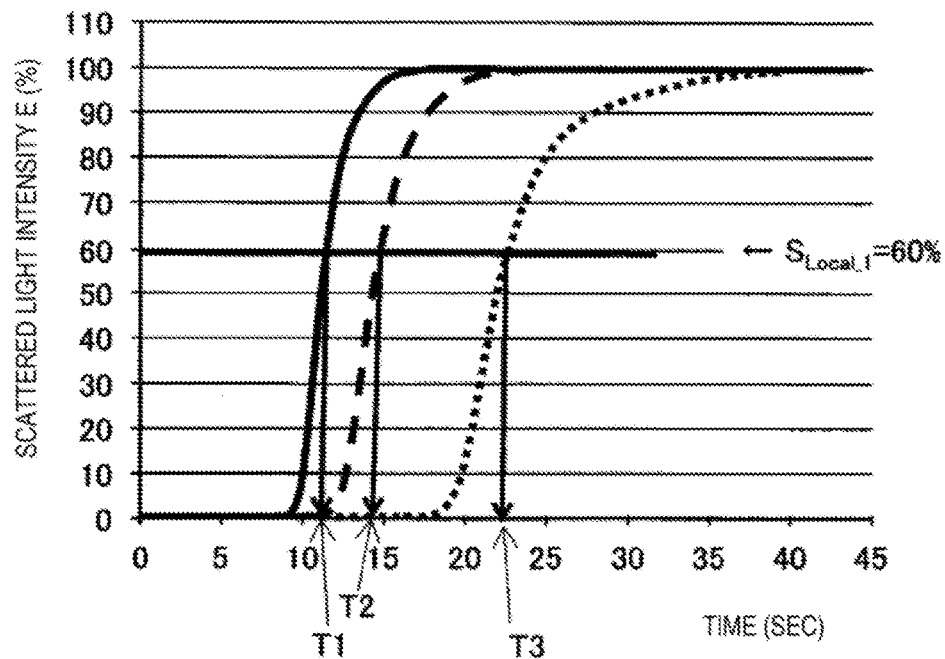
[FIG. 23B]
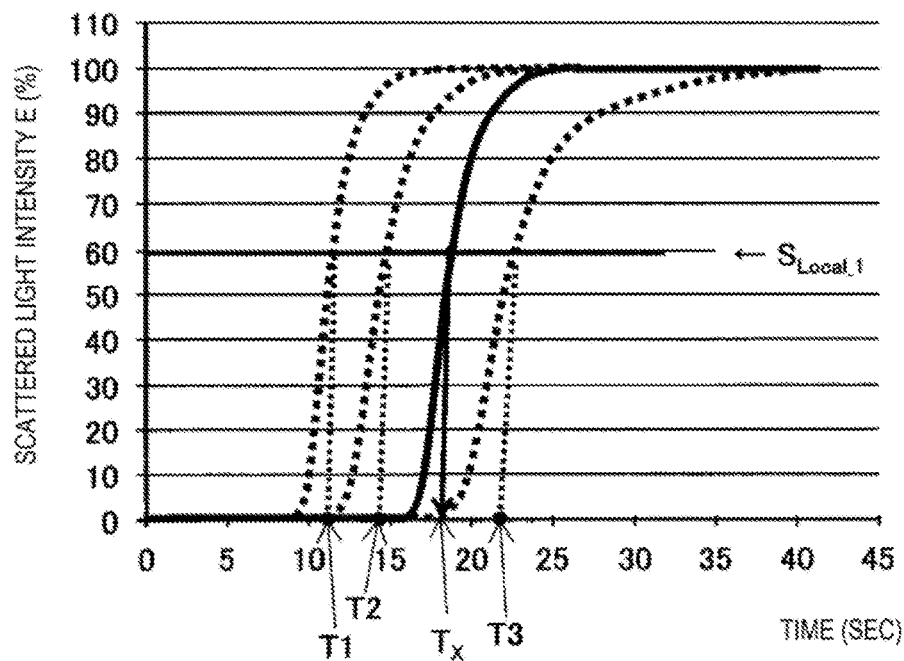

[FIG. 24A]
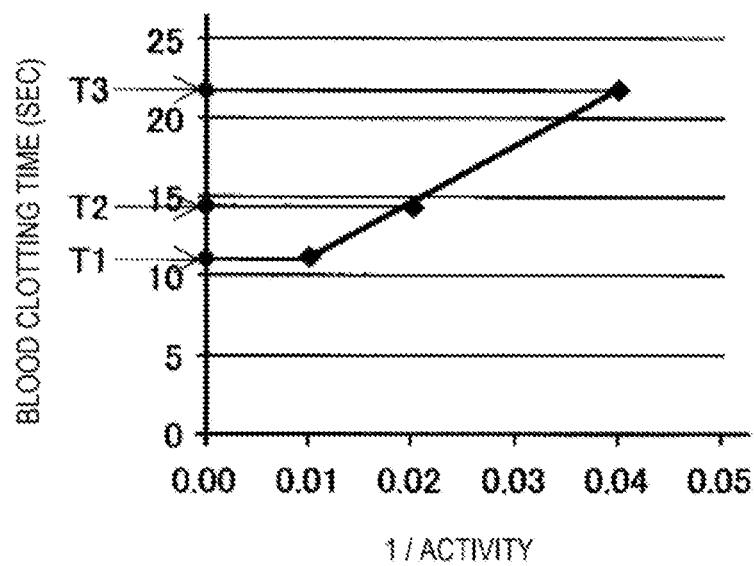
[FIG. 24B]
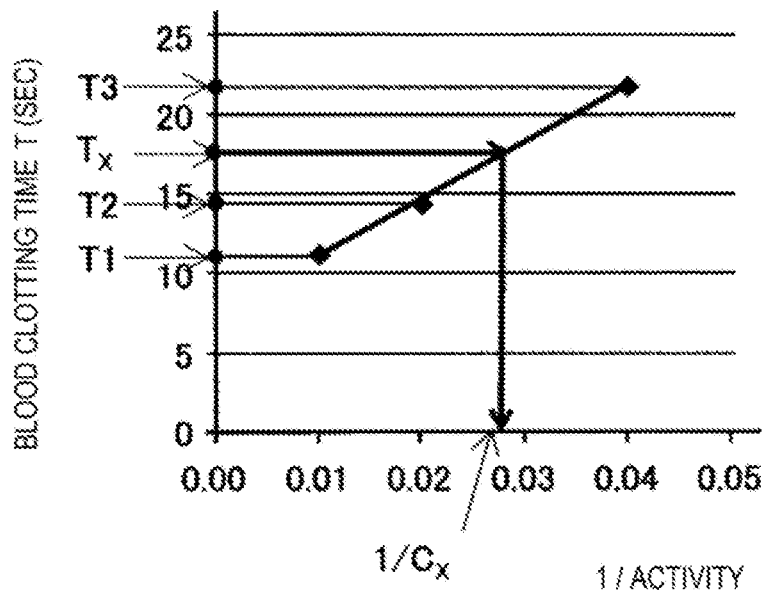

[FIG. 25A]
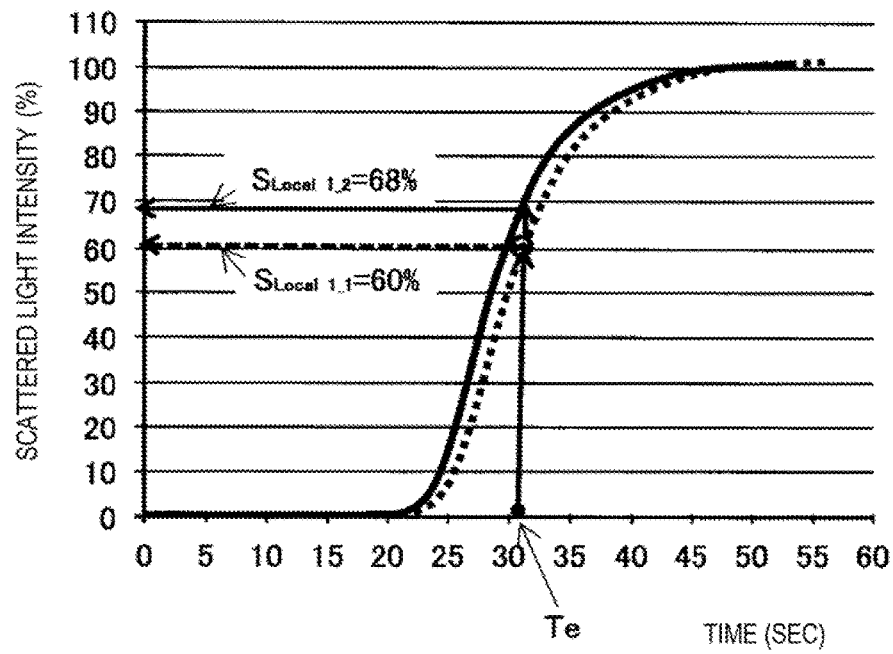
[FIG. 25B]
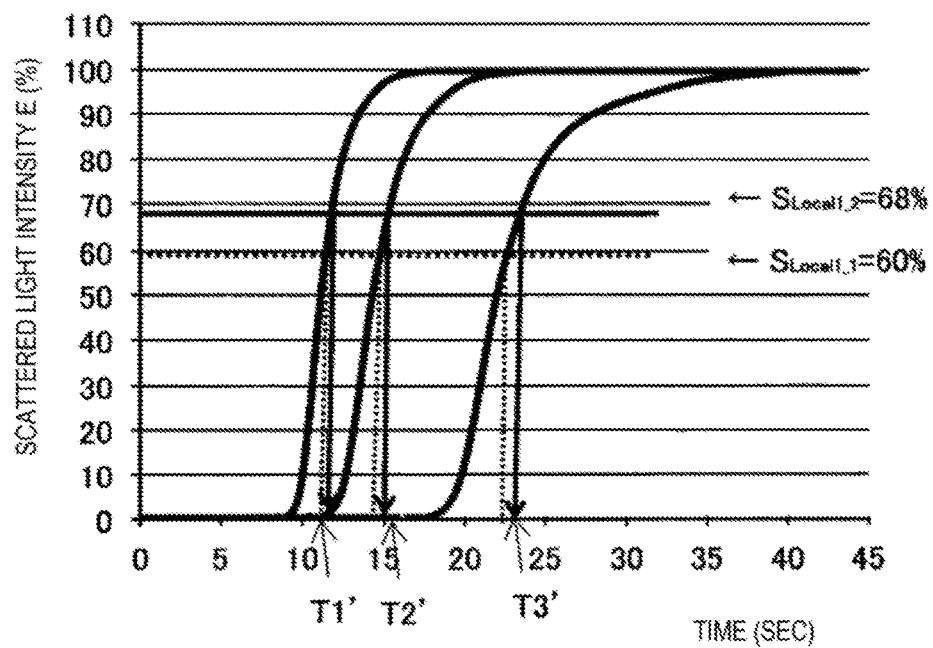

[FIG. 25C]
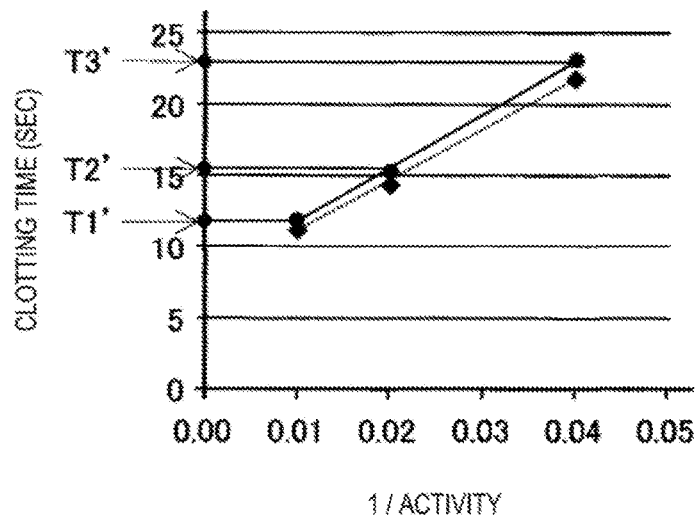
[FIG. 25D]
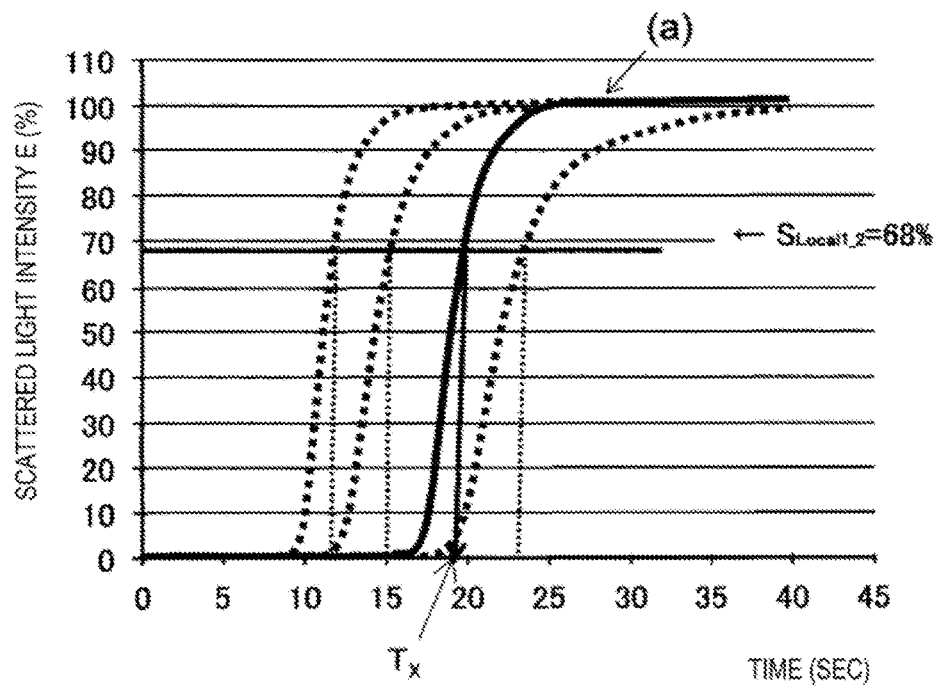

[FIG. 25E]
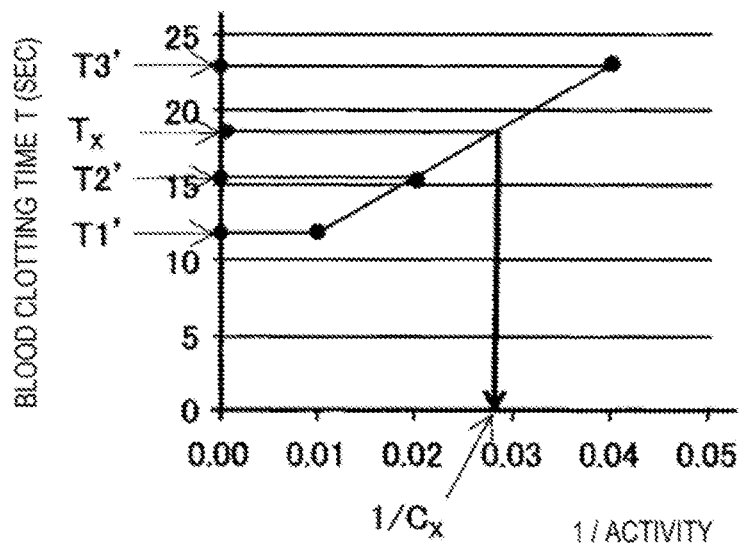
[FIG. 26]
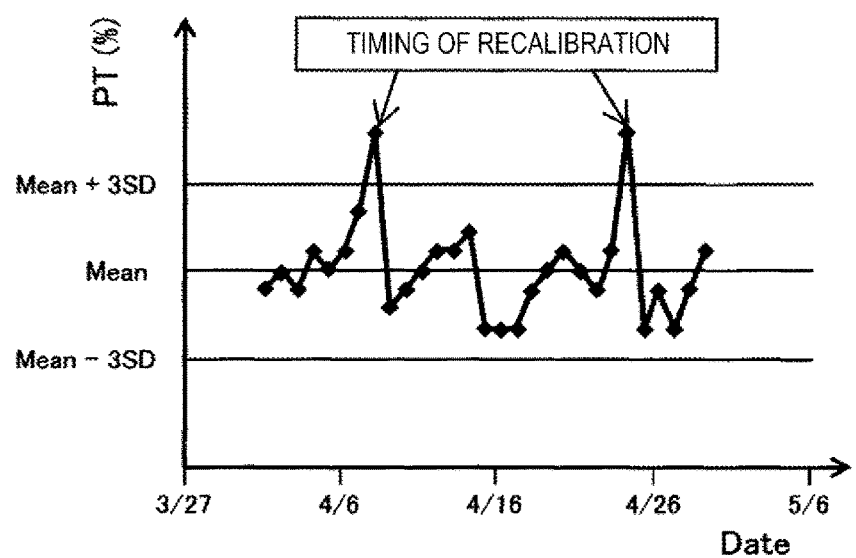

AUTOMATIC ANALYSIS DEVICE AND ANALYSIS METHOD

TECHNICAL FIELD

The present invention relates to an automatic analysis device and an analysis method for performing an analysis of a biological sample such as blood or urine, and particularly relates to a device and a method for measuring a blood clotting time or for measuring a cycle time involved in nucleic acid amplification.

BACKGROUND ART

As the automatic analysis device, there are a biochemical automatic analysis device or the like which performs a quantitative and qualitative analysis of the concentration of a component of a biological sample such as blood or urine in the field of a biochemical test or a hematological test, and the like, a blood clotting time automatic analysis device (hereinafter sometimes referred to as "blood clotting time measuring device") or the like which measures a blood clotting time, and a nucleic acid amplification test device or the like which measures a cycle time involved in nucleic acid amplification.

In the former biochemical automatic analysis device or the like, at the start of an analysis in a day or in the case where a reagent is used up, and therefore, the reagent is replaced by a reagent in a reagent vessel with a different lot number, or the like, a standard sample is measured to create a standard curve, and then, a control sample is measured, whereby an operator confirms the validity of the measured values based on the analysis result. Thereafter, a sample to be tested (which refers to a sample with an unknown concentration such as a patient specimen ordered to be tested, and is hereinafter referred to as "sample with an unknown concentration") is analyzed. In an analysis of a sample with an unknown concentration, a standard curve is created beforehand using a standard sample, and the concentration is calculated using the created standard curve. By doing this, an analysis result with no difference between facilities or no difference between reagent lots is obtained by reflecting the conditions of the device and the conditions of the reagent.

However, in the measurement of a blood clotting time by deposition of fibrin in a blood clotting test, mainly an electrical resistance detection system, an optical detection system, a mechanical system, or the like is used, and a mainstream system is an optical detection system (detection of transmitted light or detection of scattered light) or a mechanical system (detection of viscosity) having an excellent processing ability. In this manner, since the measurement system differs, even if the same item is analyzed for the same specimen, the measurement result of a blood clotting time differs. In addition, in a test reagent for a blood clotting time, a biological component is contained, and therefore, the reactivity varies depending on each lot, and therefore, the measures value of a blood clotting time varies.

As a conventional technique related to the accuracy control of sample measurement, for example, PTL 1 (Japanese Patent No. 5123496) proposes a method in which a measured blood clotting time of a specimen is converted to a standardized blood clotting time by using a standard curve plotted by assigning a standard blood clotting time having been determined beforehand and the blood clotting time of a calibration substance measured in a test system.

CITATION LIST

Patent Literature

PTL 1: Japanese Patent No. 5123496

SUMMARY OF INVENTION

Technical Problem

As described above, in a biochemical automatic analysis device or the like, when the concentration of a component is measured, standardization is generally performed such that a difference in the conditions of the device, the lot of the reagent, or the like is absorbed using a calibrated standard curve.

However, in a blood clotting time measuring device or the like, for example, in the measurement of an APTT (activated partial thromboplastin time) or the like, a measurement result is reported by a blood clotting time (sec), and therefore, reflection of the conditions of the reagent by creating a standard curve again using a standard sample as described above could not be performed. Due to this, it is more important to ascertain the conditions of the reagent using a control sample. In addition, in the case of a lyophilized reagent to be used in several items for the blood clotting test reagent, the reagent is dissolved by a user, and therefore, the conditions of the reagent differ due to a variation in the dissolving conditions even if the reagent of the same lot is used. In other words, a difference in the measurement result may sometimes occur depending on the dissolving conditions of the reagent, and therefore, also in such a case, it is more important to ascertain the conditions of the reagent using a control sample. Further, also in a nucleic acid amplification test device or the like, there is an item to report a measurement result by a reaction cycle number without creating a standard curve, and therefore, it has the same problem.

The invention has been made in view of such circumstances, and has its object to provide an automatic analysis device and an analysis method capable of improving the reliability of the measurement result by ascertaining the conditions of the reagent and the conditions of the device using a sample having a known blood clotting time (hereinafter referred to as "blood clotting time reference sample") and adjusting the measurement conditions.

Solution to Problem

In order to achieve the above object, the invention is configured to include a sample vessel placing section in which a sample vessel containing a sample to be analyzed is placed, a reagent vessel placing section in which a reagent vessel containing a reagent to be used for measuring the sample is placed, a reaction vessel in which the reagent and the sample are mixed and reacted, a sample dispensing mechanism which dispenses the sample into the reaction vessel from the sample vessel, a reagent dispensing mechanism which dispenses the reagent into the reaction vessel from the reagent vessel, a detector which detects a signal value that changes over time in accordance with the degree of the mixing reaction of the sample and the reagent, and a control section which analyzes the sample based on the result of the detection, wherein the control section includes a signal reference value setting control section which creates a reaction curve by a mixing reaction of a blood clotting time reference sample having a known blood clotting time and the reagent, and sets a signal reference value that corresponds to the blood clotting time which is an expected value having been determined beforehand based on the created reaction curve, a storage section which stores the set signal reference value and identification information having been set beforehand for the reagent in association with each other, and a processing section which determines the blood clotting time of the sample or a standard sample using the stored signal reference value, and the signal reference value setting control section creates a single reaction curve for each blood clotting time reference sample.

Advantageous Effects of Invention

According to the invention, the reliability of the measurement result can be improved by ascertaining the conditions of a reagent using a blood clotting time reference sample and setting an appropriate signal reference value for each reagent vessel.

BRIEF DESCRIPTION OF DRAWINGS

FIG. 1 is a view schematically showing the entire structure of an automatic analysis device according to a first embodiment.

FIG. 2 is a view showing one example of the change over time in the amount of scattered light detected by a detection unit in a mixing reaction of a sample and a reagent.

FIG. 3 is a view illustrating a case where a blood clotting time is calculated from a blood clotting reaction curve in a mixing reaction of a sample and a reagent.

FIG. 4 is a flow chart showing the outline of a processing procedure of a signal reference value setting process.

FIG. 5 is a view illustrating part of the procedure of the signal reference value setting process in more detail using a blood clotting reaction curve.

FIG. 6 is a view illustrating part of the procedure of the signal reference value setting process in more detail using a blood clotting reaction curve.

FIG. 7 is a view showing one example of a list of signal reference values corresponding to a plurality of reagent vessels.

FIG. 8 is a view showing an example of periodically measuring a control sample in a blood clotting time measuring device or the like to which the embodiment is not applied, and is a view showing a manner in which the blood clotting time is shifted.

FIG. 9 is a view showing an example of periodically measuring a control sample in a biochemical automatic analysis device or the like.

FIG. 10 is a view showing one example of the change over time in the amount of transmitted light detected by a detection unit in a mixing reaction of a sample and a reagent in a modification of the first embodiment.

FIG. 11 is a view illustrating a case where a Ct value is calculated from the change over time in the amount of fluorescence in a real-time PCR method in a modification of the first embodiment.

FIG. 12 is a view illustrating a relationship between a PCR reaction curve and a Ct value when using a reagent of a different lot in a modification of the first embodiment.

FIG. 13 is a view illustrating a method for setting a signal reference value in a PCR reaction curve when using a reagent of a different lot in a modification of the first embodiment.

FIG. 14 is a view showing one example of the change over time in the amount of scattered light detected by a detection unit in respective mixing reactions of a reagent and a sample at a high concentration and a low concentration.

FIG. 15 is a view illustrating a method for setting a fixed signal reference value independent of the concentration based on the mean of the values of the amount of scattered light corresponding to the respective expected values of the blood clotting time when using a sample at two concentrations.

FIG. 16 is a table showing an example of an approximate formula to be used when setting a signal reference value which is different for each concentration using a sample at a plurality of concentrations.

FIG. 17A shows a specific example of setting a signal reference value using an approximate formula with respect to the values of the amount of scattered light corresponding to the respective expected values of the blood clotting time when using a sample at a plurality of concentrations.

FIG. 17B shows a specific example of setting a signal reference value using an approximate formula with respect to the values of the amount of scattered light corresponding to the respective expected values of the blood clotting time when using a sample at a plurality of concentrations.

FIG. 17C shows a specific example of setting a signal reference value using an approximate formula with respect to the values of the amount of scattered light corresponding to the respective expected values of the blood clotting time when using a sample at a plurality of concentrations.

FIG. 17D shows a specific example of setting a signal reference value using an approximate formula with respect to the values of the amount of scattered light corresponding to the respective expected values of the blood clotting time when using a sample at a plurality of concentrations.

FIG. 17E shows a specific example of setting a signal reference value using an approximate formula with respect to the values of the amount of scattered light corresponding to the respective expected values of the blood clotting time when using a sample at a plurality of concentrations.

FIG. 18A is a view illustrating a procedure for setting a signal reference value in the case where the amounts of scattered light corresponding to the respective expected values of the blood clotting time when using a sample at two concentrations are approximated to a linear function.

FIG. 18B is a view illustrating a procedure for setting a signal reference value in the case where the amounts of scattered light corresponding to the respective expected values of the blood clotting time when using a sample at two concentrations are approximated to a linear function.

FIG. 19 is a view illustrating a procedure for calculating a blood clotting time from the reaction curve of a sample with an unknown concentration.

FIG. 20 is a flow chart illustrating a method for determining abnormality in measurement by setting the allowable range of a signal reference value in a blood clotting reaction curve.

FIG. 21 is a view illustrating an example in which a signal reference value can be set in a blood clotting reaction curve.

FIG. 22 is a view illustrating an example in which a signal reference value cannot be set in a blood clotting reaction curve.

FIG. 23A is a view illustrating a method for calculating the blood clotting time of a blood clotting time reference sample and a sample with an unknown concentration in a second embodiment.

FIG. 23B is a view illustrating a method for calculating the blood clotting time of a blood clotting time reference sample and a sample with an unknown concentration in the second embodiment.

FIG. 24A is a view illustrating a method for creating a standard curve from a relationship between the blood clotting time of a blood clotting time reference sample and the concentration thereof, and performing conversion of the concentration of a sample with an unknown concentration in the second embodiment.

FIG. 24B is a view illustrating a method for creating a standard curve from a relationship between the blood clotting time of a blood clotting time reference sample and the concentration thereof, and performing conversion of the concentration of a sample with an unknown concentration in the second embodiment.

FIG. 25A is a view illustrating a method for creating a standard curve again by setting a signal reference value, and performing conversion of the concentration of a sample with an unknown concentration in the second embodiment.

FIG. 25B is a view illustrating a method for creating a standard curve again by setting a signal reference value, and performing conversion of the concentration of a sample with an unknown concentration in the second embodiment.

FIG. 25C is a view illustrating a method for creating a standard curve again by setting a signal reference value, and performing conversion of the concentration of a sample with an unknown concentration in the second embodiment.

FIG. 25D is a view illustrating a method for creating a standard curve again by setting a signal reference value, and performing conversion of the concentration of a sample with an unknown concentration in the second embodiment.

FIG. 25E is a view illustrating a method for creating a standard curve again by setting a signal reference value, and performing conversion of the concentration of a sample with an unknown concentration in the second embodiment.

FIG. 26 is a view illustrating the diurnal/day-to-day variation of a control sample in a third embodiment.

DESCRIPTION OF EMBODIMENTS

First Embodiment

A first embodiment of the invention will be described with reference to the drawings.

In this embodiment, as one example of an automatic analysis device, a blood clotting time measuring device which measures a time from when a reagent and a biological sample (hereinafter simply referred to as "sample") such as blood or urine are mixed to when fibrin is deposited as a blood clotting time in accordance with the amount of optical change will be described.

FIG. 1 is a view schematically showing the entire structure of an automatic analysis device according to this embodiment.

In FIG. 1, an automatic analysis device 100 is roughly composed of a sample dispensing probe (sample dispensing mechanism) 101, a sample disk 102, a reagent dispensing probe (reagent dispensing mechanism) 106, a reagent disk 107, a reaction vessel container 111, a gripper 112, a detection unit 113, a waste box 117, an operation section 118, a storage section 119, and a control section 120.

The sample dispensing probe 101 sucks a sample or a blood clotting time reference sample held in a sample vessel 103 disposed on the sample disk 102 which rotates clockwise and counterclockwise, and discharges the sample into a reaction vessel 104. The sample dispensing probe 101 performs a sample suction action and a sample discharge action by the action of a sample syringe pump 105 controlled by the control section 120.

The reagent dispensing probe 106 sucks a reagent held in a reagent vessel 108 disposed on the reagent disk 107 and discharges the reagent into the reaction vessel 104. The reagent dispensing probe 106 performs a reagent suction action and a reagent discharge action by the action of a reagent syringe pump 110 controlled by the control section 120.

Inside the reagent dispensing probe 106, a reagent heating mechanism 109 is included, and the temperature of the reagent sucked by the reagent dispensing probe 106 is increased to a suitable temperature (predetermined temperature) by the reagent heating mechanism 109 controlled by the control section 120.

The gripper 112 transports and places the reaction vessel 104. The gripper 112 transports and places the reaction vessel 104 from the reaction vessel container 111 to a reaction vessel placing section 114 of the detection unit 113 by rotating in a horizontal direction while gripping the reaction vessel 104.

The detection unit 113 has one or more reaction vessel placing sections 114 for placing the reaction vessel 104 (in this embodiment, a case where the detection unit 113 has one reaction vessel placing section 114 is shown), and performs the measurement of an optical intensity of the reaction vessel 104 inserted into the reaction vessel placing section 114. Incidentally, in this embodiment, a case where one detection unit 113 is disposed is shown, however, it is not limited thereto, and the device may be configured to include a plurality of detection units 113. A light source 115 of the detection unit 113 irradiates light onto the reaction vessel 104. The light irradiated from the light source 115 is scattered by the reaction mixture in the reaction vessel 104. A detection section (light sensor) 116 is constituted by a photodiode or the like. The detection section 116 receives scattered light, which is scattered by the reaction mixture in the reaction vessel 104, converts the light to a current, and outputs the measured light signal indicating the intensity of the received scattered light to an A/D converter 121. The measured signal of the scattered light A/D-converted by the A/D converter 121 is input to the control section 120 through an interface 122. The action of the detection unit 113 is controlled by the computer 120 for control.

The gripper 112 grips the reaction vessel 104 after completion of the measurement and disposes of the reaction vessel 104 in the waste box 117.

An analysis item for a sample to be analyzed by the automatic analysis device 100 is input to the control section 120 from the operation section 118 through a keyboard 118b as an input unit or an operation screen displayed on a display section 118c. Incidentally, the device may be configured to use a GUI (Graphical User Interface) for inputting an analysis item by operating an analysis item displayed on the display section 118c with a pointer or the like using a mouse 118a.

The control section 120 includes an overall control section 120a, a measurement control section 120b, and a signal reference value setting control section 120c.

The overall control section 120a controls the action of the automatic analysis device such as dispensing of the sample or the reagent, transfer of the reaction vessel 104, disposal of the reaction vessel 104, or the like.

The measurement control section 120b performs a measurement process for measuring the reaction time of a sample based on the result of comparison between a signal reference value having been determined beforehand and a light intensity (signal value) which changes over time in accordance with the degree of the mixing reaction of the sample and the reagent. Incidentally, the signal value in this embodiment is a scattered light intensity, and the blood clotting time of the sample is calculated based on the measured light signal from the detection unit 113. The calculated blood clotting time is output to the display section 118*c* and also stored in the storage section 119. Incidentally, the clotting time as the calculation result may be printed and output by a printer 123 through the interface 122.

The signal reference value setting control section 120*c* performs a signal reference value setting process (which will be described later) for setting a signal reference value such that the blood clotting time measured based on the result of comparison between the signal reference value and the signal value (scattered light intensity) which changes over time in accordance with the mixing reaction of a blood clotting time reference sample or the like and a reagent corresponds to the expected value of the blood clotting time having been determined beforehand as corresponding thereto. Here, the signal reference value in the calculation of the blood clotting time refers to the ratio on the basis of which blood clotting is determined when normalization is performed by taking the amount of light at the start of the reaction as 0 and the optical change until completion of the reaction as 100. That is, the time when the amount of light exceeds the ratio (signal reference value) having been determined beforehand is defined as the blood clotting time. The determined signal reference value set by the signal reference value setting control section 120*c* and the identification information having been set beforehand for the reagent are stored in the storage section 119 as the corresponding information.

Here, a method for calculating the blood clotting time in the measurement process in this embodiment will be described.

FIG. 2 is a view showing one example of the change over time in the amount of scattered light detected by the detection unit 113 in the mixing reaction of the sample and the reagent.

In this embodiment, the blood clotting time is calculated from the blood clotting reaction curve of the signal value measured over time by the detection section. In the blood clotting reaction, when a sample and a given reagent are discharged into the reaction vessel 104 placed in the reaction vessel placing section 114 by the reagent dispensing probe 106, a blood clotting reaction starts as the mixing reaction. That is, the action of discharge of the reagent by the reagent dispensing probe 106 serves as the starting point, and the blood clotting reaction is started (time: t=t0).

In the blood clotting reaction curve shown in FIG. 2, the scattered light intensity E reaches a fixed minimum value Eb from the start of the measurement (time: t=t0) to the time t=t1, the scattered light intensity E increases from the time t=t1 to the time t=t2, and the scattered light intensity E reaches a fixed maximum value Ep when the time t is t2 and thereafter.

In such a blood clotting reaction curve, a region in which the scattered light intensity E reaches the fixed minimum value Eb refers to a base line region, and a region in which the scattered light intensity E reaches the fixed maximum value Ep refers to a plateau region.

In the measurement process of the blood clotting reaction, when normalization is performed with respect to the change in the amount of scattered light between the time t=t1 and the time t=t2 by taking the scattered light intensity in the base line region as 0% and the scattered light intensity in the plateau region as 100%, the time when the ratio (the signal reference value S) having been determined beforehand is exceeded is defined as the blood clotting time T.

Next, a method for calculating a blood clotting time Ta when the measurement is performed using the reagent of a lot A and a blood clotting time Tb when the measurement is performed using the reagent of a lot B will be described with reference to FIG. 3. When the blood clotting reaction curve is normalized by taking the scattered light intensity in the base line region as 0% and the scattered light intensity in the plateau region as 100%, and the signal reference value S is set to 50%, the blood clotting time Ta is 31.5 sec. Here, the reactivity differs when the lot of the reagent is changed, and therefore, even in the case where the same sample is measured, the blood clotting reaction curves do not necessarily overlap each other. For example, in FIG. 3, in the case where the measurement is performed using the reagent of a lot B, the blood clotting time Tb calculated from the blood clotting reaction curve is 32.0 sec. This indicates that a difference in the measurement result occurs depending on the lot of the reagent even in the case where the same sample is measured, and in this embodiment, a method for decreasing the variation in the measured value by minimizing the difference.

Next, a method for setting the signal reference value in the signal reference value setting process of this embodiment will be described.

FIG. 4 is a flow chart showing the outline of a processing procedure of a signal reference value setting process. Further, FIGS. 5 and 6 are views illustrating part of the procedure of the signal reference value setting process in more detail using a blood clotting reaction curve.

In FIG. 4, it is necessary to confirm whether or not the conditions of the device or the reagent are favorable before the measurement. As a method for confirming the conditions of the device or the reagent, for example, after confirming the temperature of the detector or the reagent probe with a heating function (S401), the measurement is performed using a control sample (S402). In the case where the conditions of either or both of the device and the reagent are not favorable, it is necessary to improve the conditions so that favorable conditions are obtained by performing the maintenance of the device or replacing the reagent (S403). On the other hand, in the case where the conditions of both are favorable as a result of confirmation in S401 and S402, it is determined whether or not the measured value of the blood clotting time reference sample calculated using the current signal reference value $S_{Local}$ which is the initial value having been set beforehand is in a predetermined range in Step 404 (S404). In the case where the measured value is in the predetermined range, in Step 405, setting is performed so that the current signal reference value $S_{Local}$ is continued to be used (S405). On the other hand, in the case where the measured value is outside the predetermined range, in Step 406, the signal reference value setting control section 120*c* reads the range of variation and the expected value (Te) of the blood clotting time in the case where the blood clotting time reference sample is measured using the reagent to be used in the signal reference value setting process in the blood clotting time measuring device to serve as a reference (Step S406).

Here, in the case where the measured value of the blood clotting time reference sample obtained using the current signal reference value $S_{Local}$ in S404 is in the allowable range, it is not necessary to reset the signal reference value.

Subsequently, in Step 407, in the blood clotting time measuring device to be used for the signal reference value setting process, the measurement of the blood clotting time reference sample is performed using the reagent to be used for setting the signal reference value, whereby a blood clotting reaction curve (see FIG. 5) is obtained (Step S407).

Subsequently, in Step 408, the signal reference value $S_{Local}$ at which the blood clotting time calculated by applying the expected value Te of the blood clotting time with respect to the blood clotting reaction curve (see FIG. 5) obtained in S407 corresponds to the expected value Te is set (see FIG. 6, S408).

Then, in Step 409, the signal reference value $S_{Local}$ obtained in S408 is stored in the storage section 119 as the information corresponding to the reagent used in the signal reference value setting process (S409).

In the measurement of the sample with an unknown concentration thereafter, in the case where the reagent of the same lot as that of the reagent used in the signal reference value setting process is used, the signal reference value $S_{Local}$ in the storage section 119 is read and used. Incidentally, in this embodiment, with respect to the reagent of the same lot, the same signal reference value $S_{Local}$ is used, however, the corresponding signal reference value $S_{Local}$ may be determined each time by performing the signal reference value setting process with respect to each reagent vessel. In this case, the reliability of the measurement result can be further improved. The method for controlling the signal reference value for each reagent vessel will be described later.

Incidentally, in the blood clotting time measuring device to serve as a reference, as for the calculation of the range of variation and the expected value Te of the blood clotting time in the case where the blood clotting time reference sample to be used in the signal reference value setting process is measured, by performing the same measurement a plurality of times, a mean, a median, or the like of the calculated blood clotting time in combination of a specific reagent and the blood clotting time reference sample is defined as the expected value Te, and a standard deviation, a dispersion, or the like thereof is given as the range of variation. Incidentally, in the calculation of the expected value Te and the range of variation in this measurement, it is desired to perform the calculation in consideration of a diurnal or day-to-day variation. Further, it is preferred that with respect to the blood clotting time measuring device to serve as a reference, in consideration of the machine difference between specified device types, the status of accuracy control for each facility is controlled by a network as to whether the measurement is repeated by a plurality of devices, and the measurement results of the devices in a plurality of facilities are aggregated and reflected.

According to the procedure as described above, the difference between devices with respect to an item (for example, APTT: activated partial thromboplastin time) that treats the calculated blood clotting time as the measurement result as it is without creating a standard curve is corrected.

In general, in the field of blood testing, a value is determined by a combination of the reagent of the same lot and the sample. In particular, in the blood clotting test, a reagent containing a biological component is used as the reagent in some cases, and in such a case, a lot-to-lot difference is large, the sensitivity to a chemical is greatly varies for each reagent, and so on. Therefore, standardization is not achieved. However, even in the case of such an item, if the combination is a combination of the reagent of the same lot and the sample, the expected value of the result measured in the specified device can be uniquely determined. That is, the reagent sufficiently tested at the time of shipping and the blood clotting time reference sample can define the expected value and the range of variation of the blood clotting time by the combination of the sample with a variety of reagents.

Here, the control of the signal reference value $S_{Local}$ for each reagent vessel will be described.

FIG. 7 is a view showing one example of a list of signal reference values corresponding to a plurality of reagent vessels.

In FIG. 7, with respect to the reagent vessel 108 placed at each position of the reagent disk 107, the item, the lot number of the reagent, and the lot number of the blood clotting time reference sample are listed, and a case where an intrinsic signal reference value is made to correspond to each reagent vessel is shown. In the case where a plurality of reagent vessels are placed for the same item, the signal reference value is shown independently. The item which has not been measured can be made identifiable on the operation screen. Preferably, when the measurement is requested, the number of requests and the number of remaining tests are confirmed, and in the case where a reagent bottle for which the signal reference value has not been set is planned to be used, a warning that the signal reference value has not been set is issued from the control section 120. Further, it is also considered that even in the case where the signal reference value has not been set, when an operator gives permission, the same signal reference value as the signal reference value of another reagent vessel is set. In the case of APTT reagents at position 1 and position 2, the reagent vessels are different, however, the lot numbers are both A00001, and therefore, a common signal reference value for each lot can be set. In the case of PT reagents at position 4 and position 5, the lot numbers are B00001 and B00002 and are different, and therefore, different signal reference values are set. However, in the case where even if the lot numbers are the same, different signal reference values are desired to be set, it is possible to set the signal reference values for the reagent vessels. For example, the reagents at position 5 and position 6 show a case where although the lot numbers are the same, different signal reference values are set for each reagent vessel is shown. This is because even in the case of the reagents of the same lot, the reactivity sometimes differs depending on the storage conditions of the reagent or the like, and therefore, it is effective that the signal reference value is controlled for each reagent vessel. Further, position 3 and position 8 show a case where the signal reference value has not been set.

The action in this embodiment configured as described above will be described.

In the signal reference value setting process in the blood clotting time measuring device which is the automatic analysis device according to this embodiment, first, an operator obtains the expected value Te and the range of variation of the blood clotting time through a bar code attached to the reagent, a network, or a method of reading or the like in the package insert of the reagent (Step S406 in FIG. 4). Preferably, it is desired that the identification information such as a bar code attached to the reagent is read and the information corresponding to the reagent is obtained through a network, whereby the information is directly incorporated in the storage section 119 of the blood clotting time measuring device to be used for the signal reference value setting process. However, in the case where the direct incorporation cannot be performed, the operator can manually input the information from the operation section 118.

Here, the error of the measurement result in a clinical test leads to a diagnostic error, and therefore, it is an essential requirement that the validity of the measurement result is confirmed. In the automatic analysis device or the like, it is a general rule that the validity of the measurement result is confirmed by performing measurement using a control sample periodically in addition to when the reagent lot is changed. The variation using the control sample in the biochemical automatic analysis device or the like is, for example, controlled as shown in FIG. 9. FIG. 9 shows an example of periodically measuring a control sample. Here, the "Mean" indicates a case where a mean determined for each device type is defined as the expected value, and as for the range of variation with respect to the Mean, ±3SD is defined as the allowable range. Here, the "Mean" and the "SD" are preferably the results calculated by a plurality of reference devices or the values obtained by aggregating the measurement results in a plurality of facilities.

On the other hand, with respect to an item to report the measurement result by the blood clotting time (sec) without creating a standard curve such as the measurement of an APTT (activated partial thromboplastin time), the difference between devices is not corrected by calibration, and therefore, a difference between devices occurs even if the device type is the same, and the blood clotting time does not necessarily match the mean determined for each device type. FIG. 8 shows an example of periodically measuring a control sample in a blood clotting time measuring device or the like to which this embodiment is not applied. In such a case, it is not suitable to set the range of variation of the mean determined for each device type to ±3SD, and therefore, it is necessary to correct the difference between devices of the mean.

The correction of the difference between devices can be performed by setting the signal reference value for calculating the blood clotting time in the blood clotting reaction curve for each facility and for each reagent vessel.

Further, as for the timing of the signal reference value setting process, the signal reference value setting process is preferably performed when a new reagent vessel is placed and for each item when the blood clotting time reference sample is measured. At this time, the signal reference value $S_{Local}$ is set (Steps S407 and S408 in FIG. 4).

Subsequently, when an operator performs an analysis of a sample with an unknown concentration, in the control section 120, the content of the measurement is confirmed, and a sample and a reagent to be used, and a position where the measurement is performed are allocated. A time when the change in the light intensity exceeds $S_{Local}$ is calculated as the blood clotting time from the obtained measurement result.

The effect of this embodiment configured as described above will be described.

As described above, for example, in the measurement of an APTT (activated partial thromboplastin time), reflection of the conditions of the reagent by creating a standard curve again cannot be performed, and therefore, it is more important to ascertain the conditions of the reagent using a blood clotting time reference sample. In addition, in the case of a lyophilized reagent to be used in several items for the blood clotting test reagent, the reagent is dissolved by a user, and therefore, the conditions of the reagent differ due to a variation in the dissolving conditions even in the case of the reagent of the same lot. In other words, a difference in the measurement result may sometimes occur depending on the dissolving conditions of the reagent, and therefore, it is more important to ascertain the conditions of the reagent using a control sample for each reagent vessel.

On the other hand, this embodiment is configured such that the difference between devices is corrected by performing the setting of the signal reference value that corresponds to the expected value of the blood clotting time having been determined beforehand as corresponding to the blood clotting time reference sample using a blood clotting reaction curve which changes over time in accordance with the mixing reaction of a blood clotting time reference sample and a reagent, and therefore, the conditions of the reagent are more easily ascertained using the blood clotting time reference sample, and the reliability of the measurement result can be improved.

Modification of First Embodiment

A modification of the first embodiment of the invention will be described.

In the first embodiment, a change in scattered light intensity is illustrated as the blood clotting reaction curve, however, in this modification, a case where a change in transmitted light is used as the blood clotting reaction curve is shown.

FIG. 10 is a view showing one example of the change over time in the amount of transmitted light detected by the detection unit 113 in the mixing reaction of a sample and a reagent in the modification.

In the modification of this embodiment, a blood clotting time is calculated from a blood clotting reaction curve measured over time by the detection section. In a blood clotting reaction, when a given reagent is discharged into the reaction vessel 104 which held a sample and placed in the reaction vessel placing section 114 by the reagent dispensing probe 106, a blood clotting reaction starts as the mixing reaction. That is, the action of discharge of the reagent by the reagent dispensing probe 106 serves as the starting point, and the blood clotting reaction is started (time: t=t0).

In the blood clotting reaction curve shown in FIG. 10, the transmitted light intensity E reaches a fixed maximum value Es from the start of the measurement (time: t=t0) to the time t=t1, the transmitted light intensity E decreases from the time t=t1 to the time t=t2, and the transmitted light intensity E reaches a fixed minimum value Ee when the time t is t2 and thereafter.

In the measurement process of this blood clotting reaction, when the change in the amount of transmitted light between the time t=t1 and the time t=t2 is taken as 100%, the time when the ratio (the signal reference value S) having been determined beforehand is exceeded is defined as the blood clotting time T.

The other configuration is the same as that of the first embodiment.

Also in this modification configured as described above, the same effect as that of the first embodiment can be obtained.

Incidentally, also in a genetic testing device represented by a real-time PCR device, the basic structure is the same as that of the first embodiment or this modification, and this technique can be applied by replacing the light intensity to be measured over time by a fluorescence intensity, and representing the cycles on the horizontal axis.

That is, in the field of genetic testing, by a nucleic acid amplification method, a very small amount of a virus or a bacterium is amplified so as to be able to be detected, whereby a disease is determined. A most common example of the nucleic acid amplification method is a PCR (Polymerase Chain Reaction) method. In a common PCR method, a DNA is amplified two-fold by changing the temperature in one cycle consisting of three steps of thermal denaturation, annealing, and extension. When a double-stranded DNA is denatured into single strands in the thermal denaturation step, a primer having a sequence complementary to a target nucleic acid can bind to the target nucleic acid in the annealing step. In the subsequent extension step, a double-stranded cDNA is synthesized by the action of a DNA synthase. By repeating this cycle, the target DNA is amplified exponentially.

In recent years, among the PCR methods, a real-time PCR method which is simple and has high accuracy has been widely used. The real-time PCR method is a method in which a probe or the like attached with a fluorescent dye is used when performing PCR and a DNA is detected by measuring a fluorescence intensity while amplifying the DNA, and the fluorescence intensity is enhanced as the DNA is amplified. Here, the determination of amplification in the real-time PCR method is performed by calculating the cycles (Ct value: Threshold Cycle Value) when a signal reference value having been determined is exceeded. In particular, in a quantitative test, a standard curve is created from a relationship between the Ct value and the concentration of a sample with a known concentration, for example, a standard sample, and the sample with an unknown concentration is quantitatively determined.

However, in the real-time PCR method, other than quantitative measurement, genotyping, qualitative analysis, and the like can be performed, and for these items, the Ct value is reflected in the measurement result as it is without creating a standard curve.

FIG. 11 is a view illustrating a method for calculating a Ct value in a real-time PCR method, and shows an example of a PCR reaction curve in the case where the measurement is completed after 60 cycles. In FIG. 11, the start of the measurement is defined as a 1st cycle, the end of the measurement is defined as a 60th cycle, and when normalization is performed by taking the amount of fluorescence at the start of the measurement as 0% and the change in the amount of fluorescence until the completion of the measurement as 100%, the cycle number at the time when the ratio (the signal reference value S) having been determined beforehand is exceeded is defined as the Ct value.

FIG. 12 is a view illustrating a method for calculating $Ct_a$ which is a Ct value when the measurement is performed using the reagent of a lot A and $Ct_b$ which is a Ct value when the measurement is performed using the reagent of a lot B. When normalization is performed by taking the fluorescence intensity in the base line region of the PCR reaction curve as 0% and the fluorescence intensity in the plateau region as 100%, and the signal reference value S is set to 20, $Ct_a$ is 28.0. Here, the reactivity differs when the lot of the reagent is changed, and therefore, even in the case where the same sample is measured, the PCR reaction curves do not necessarily overlap each other. For example, in FIG. 12, in the case where the measurement is performed using the reagent of a lot B, $Ct_b$ calculated from the PCR reaction curve is 29.8. In such a case, when the expected Ct value ($Ct_e$) having been defined beforehand is used, the variation in the measured value depending on the low can be reduced. Specifically, the method is the same as the flowchart shown in FIG. 4, and therefore, a detailed description will be omitted, however, the flowchart can be applied by replacing the Te value which is the expected value of the blood clotting time in FIG. 4 by the $Ct_e$ value which is the expected value in the PCR reaction. In the example in FIG. 13, in the case where $Ct_e$ is 27.5, the signal reference values $S_{Locala}$ and $S_{Localb}$ obtained from the PCR reaction curves when measurement is performed using the reagent of a lot A and the reagent of a lot B can be set to 12.5% and 7.5%, respectively.

On the other hand, as another example of the nucleic acid amplification method, there is a method in which a reaction is allowed to proceed at a fixed temperature without actively changing the temperature unlike the PCR method. Examples thereof include constant temperature amplification methods such as a LAMP (loop-mediated isothermal amplification) method and a TRC (transcription-reverse transcription concerted) method. The amplification in the constant temperature amplification method can be detected by measuring a fluorescence intensity or a turbidity at fixed intervals concurrently with amplification in the same manner as real-time PCR. In the detection, a method in which a fluorescent dye having a primer or a specific sequence which binds to a target nucleic acid, a fluorescent dye which directly intercalates into a DNA, or the like is added, and fluorescence is detected is generally used, however, as the LAMP method, there is also a method in which a byproduct produced accompanying the amplification of a nucleic acid is detected by turbidity or fluorescence. In the constant temperature amplification method, a result is often calculated by a qualitative analysis, and in such a case, a standard curve is not created in some cases. Since a time T when a given turbidity or fluorescence intensity is exceeded is used in place of the Ct value, it is possible to set the signal reference value by replacing the cycle number in FIG. 13 by the amplification start time T.

In this manner, the invention can be applied in the same manner as the first embodiment also to an analysis item for which a time or a cycle number at which the signal reference value is exceeded is calculated as the measurement result from the amount of change in the measured signal value (the amount of transmitted light, the amount of scattered light, the amount of fluorescence, or the turbidity).

Another Modification of First Embodiment

Another modification of the first embodiment of the invention will be described.

In the first embodiment, a method for setting a signal reference value using a blood clotting time reference sample at one concentration is shown, however, in this modification, a case where the measurement is performed using a plurality of blood clotting time reference samples such as a high-concentration sample and a low-concentration sample having different reactivity is shown.

FIG. 14 is a view showing one example of the change over time in the amount of scattered light detected by the detection unit 113 in the respective mixing reactions of a reagent and a sample at a high concentration and a low concentration.

In FIG. 14, when the expected value of the blood clotting time for the high-concentration sample is represented by T1 and the expected value of the blood clotting time for the low-concentration sample is represented by T2, a signal reference value ($S_{Local\_high}$) which matches the expected value T1 and a signal reference value ($S_{Local\_low}$) which matches the expected value T2 are determined from a blood clotting reaction curve obtained in the automatic analysis device which measures the blood clotting time. At this time, the value of the signal reference value $S_{Local}$ to be used in the calculation of the blood clotting time is used as the mean of the respective signal reference values (FIG. 15).

Further, as a more complicated example, an approximate straight line is formed with respect to a plurality of signal reference values and blood clotting times obtained from the reaction curves of a plurality of blood clotting time reference samples, and a signal reference value which is different for each concentration can also be set.

Examples of an approximate formula include a formula obtained by linear approximation, polynomial approximation, logarithmic approximation, or exponential approximation of a plurality of calculated signal reference values (FIGS. 16, and 17A to 17D). Further, there is also a method in which a plurality of calculated signal reference values are connected with broken lines, each of which is approximated by a linear function (FIG. 17E). Here, an approximation method using the linear function: Y=aT+b will be described in detail with reference to FIG. 18.

In FIG. 18A, with respect to the expected value T1 (30 sec) of the blood clotting time for the high-concentration sample and the expected value T2 (50 sec) of the blood clotting time for the low-concentration sample, the intersection points thereof with the respective blood clotting reaction curves are 68% and 60%, respectively. At this time, as shown in FIG. 18B, from a straight line obtained by connecting the above two intersection points, a slope a and an intercept b are obtained, and the formula: $S_{Local}=0.4T+48$ can be derived.

FIG. 19 is a view illustrating a method for calculating the concentration of an unknown sample at this time. That is, a value on the X axis of the intersection point A between a reaction curve (a reaction curve (a) in FIG. 19) obtained by measuring the unknown sample and the $S_{Local}=0.4T+48$ calculated in FIG. 18 is the blood clotting time T.

As described above, when the measurement is performed using a device in each facility, in a combination of a reagent having been sufficiently tested and a blood clotting time reference sample, by setting an intrinsic signal reference value $S_{Local}$ for each reagent vessel, an accurate blood clotting time can be calculated without difference between devices or difference between reagent vessels.

Incidentally, the allowable range of the signal reference value in this embodiment is limited to a range in which the amount of light changes (a range of the amount of light from 0% to 100%), more preferably limited to a range from 5% to 95%. According to this embodiment, by setting the allowable range of the signal reference value $S_{Local}$ and the allowable range of the blood clotting time reference sample for each item beforehand, it can be determined whether or not the measurement result of the blood clotting time reference sample is in the allowable range, and in the case where the measurement result largely exceeds the allowable range, a system alarm is issued, and it is possible to propose a retest or to make the reagent unusable.

The procedure for issuing a system alarm is shown in a flow chart in FIG. 20. First, in Step 2001, the expected value Te and the range of variation of the blood clotting time are obtained by a method such as reading or the like of a bar code attached to the reagent, a network, or the description of the package insert of the reagent (S2001). Subsequently, in Step 2002, by measuring a blood clotting time reference sample, a blood clotting reaction curve is obtained (S2002). Here, in Step 2003, the blood clotting times $T_{max}$ and $T_{min}$ for the upper limit and the lower limit of the allowable signal reference value having been set beforehand are calculated (S2003), and in Step 2004, it is determined whether or not the expected value Te of the blood clotting time satisfies the following relationship: $T_{min}<Te<T_{max}$ (S2004). Here, in the case where Te satisfies the conditions of the range, in Step 2005, the signal reference value $S_{Local}$ at which the blood clotting time becomes Te is set (S2005), and in Step 2006, the signal reference value $S_{Local}$ is stored in the storage section (S2006), whereby it is used for the calculation of the blood clotting time of a sample with an unknown concentration.

On the other hand, in the case where the expected value Te of the blood clotting time does not satisfy the following relationship: $T_{min}<Te<T_{max}$, in Step 2007, a system alarm that the signal reference value cannot be set is issued (S2007).

Specific examples are shown in FIGS. 21 and 22. FIG. 21 shows an example in which the signal reference value can be set. Here, when the lower limit of the signal reference value is set to 30%, the upper limit of the signal reference value is set to 70%, and the expected value Te is set to 31.5 sec, the blood clotting times when the signal reference value is 30% and 70% are as follows: $T_{min}=29.0$ sec and $T_{max}=34.5$ sec. This case satisfies the following relationship: $T_{min}<Te<T_{max}$, and therefore, the signal reference value at which the blood clotting time becomes Te can be calculated, and the signal reference value $S_{Local}$ is 49%.

FIG. 22 shows an example in which the setting of the signal reference value is failed. Here, the lower limit of the signal reference value is set to 30%, the upper limit of the signal reference value is set to 70%, and the expected value Te is set to 31.5 sec. The blood clotting times when the signal reference value is 30% and 70% are as follows: $T_{min}=32.5$ sec and $T_{max}=37.0$ sec, and therefore, Te is smaller than $T_{min}$, and thus, the relationship in S2004 is not satisfied. Accordingly, the signal reference value at which the blood clotting time becomes Te cannot be calculated. In this case, in the reaction curve of the blood clotting time reference sample, Te is outside the variable range of the signal reference value, and therefore, any of the blood clotting time reference sample, the reagent, and the device may have a problem, and thus, a system alarm is issued to notify of abnormality.

In this manner, by setting the allowable range of the signal reference value beforehand, it is possible to notify of abnormality in measurement.

Second Embodiment

A second embodiment of the invention will be described with reference to the drawings.

This embodiment is configured to apply the first embodiment to the confirmation of the validity of the preparation of a reagent in the case of a lyophilized reagent.

For example, in a reagent for measuring a prothrombin time (hereinafter referred to as "PT"), a tissue thromboplastin derived from an animal is contained, and in order to maintain stability, a lyophilized reagent is usually used. Conventionally, the lyophilized reagent is dissolved manually by a laboratory technician, and therefore, there was a problem that a variation in the measured value due to the preparation error cannot be controlled in the device. On the other hand, in order to mount a function to prepare a reagent on the device, a mechanism for dispensing a solution and a mechanism for stirring the solution are needed, and therefore, there was a problem that the size of the device is increased and also the cost is increased. Therefore, by setting a signal reference value $S_{Local}$ for each reagent vessel as described above even if the lot is the same, a measurement result can be obtained without creating a standard curve by setting a signal reference value for each reagent vessel without measuring a standard sample with respect to the reagent prepared by the same method.

Here, a procedure when a calibration result obtained by measurement in a reagent vessel 1 using a reagent of a lot A and a blood clotting time reference sample of a lot B is taken over to a reagent vessel 2 will be described. FIG. 23A is a view illustrating a method for calculating the blood clotting time of the blood clotting time reference sample from a signal reference value having been set beforehand in the case where the analysis item is a PT, and FIG. 24A is an explanatory view showing a method for creating a standard curve from the calculated blood clotting time.

First, with respect to the measurement result obtained using the reagent of a lot A and the blood clotting time reference sample of a lot B, the information of the expected value Te and the range of variation of the blood clotting time is read and obtained from the bar code of the reagent, a network, or the package insert of the reagent. Subsequently, by using the reagent of the lot A in the reagent vessel 1, the blood clotting time reference sample of the lot B is measured, and a signal reference value $S_{Local\_1}$ is set (see FIG. 6). Subsequently, the blood clotting time reference sample at three concentrations is measured in the reagent vessel 1, and blood clotting times T1 to T3 calculated using a blood clotting reaction curve and the signal reference value $S_{Local\_1}$ are obtained (see FIG. 23A). Plotting is performed on a graph using the obtained T1 to T3, whereby a standard curve is created (see FIG. 24A).

In the case where a sample with an unknown concentration is measured in the reagent vessel 1, a blood clotting time Tx is calculated using the signal reference value $S_{Local\_1}$ (FIG. 23B), and Tx is applied to the standard curve, and the concentration Cx of the sample with an unknown concentration is calculated (FIG. 24B). Subsequently, the residual amount of the sample with an unknown concentration in the reagent vessel 1 is decreased, and it is taken into account that the reagent vessel 1 will be replaced by a reagent vessel 2 of the same lot (lot A), and an analysis is performed.

In the past, in the case where the labor and cost for performing calibration again were considered, when the measurement result of a sample were in the allowable range, the calibration result of the reagent vessel 1 was taken over without performing calibration. However, in the reagent vessel 2, the reactivity differs from that in the reagent vessel 1 in a strict sense due to a difference in the amount of water for dissolving the lyophilized reagent or a difference in the storage stability, and therefore, a small difference may occur in some cases.

According to this embodiment, a more accurate measurement result can be obtained by setting a signal reference value which is different for each reagent vessel from the measurement result of a blood clotting time reference sample even without performing calibration. Also in this case, it is a prerequisite that the range of variation of the signal reference value is in a predetermined range in which the measured value of the blood clotting time reference sample calculated using the same is allowable, and therefore, with respect to the value outside this predetermined range, the signal reference value $S_{Local}$ should not be set. In such a case, according to the flow chart in FIG. 20, it is desired to issue a system alarm.

According to this embodiment, by setting the allowable range of $S_{Local}$ for each item beforehand, it can be determined whether or not the measurement result of the blood clotting time reference sample is in the allowable range, and in the case where the measurement result is outside the allowable range, an alarm is issued, and it is possible to propose the confirmation of the conditions of the reagent and the conditions of the device.

Here, a case where the signal reference value obtained from the blood clotting reaction curve of the blood clotting time reference sample is in the allowable range of variation is assumed, and the creation of a standard curve for the reagent vessel 2 and the calculation of the concentration of a sample with an unknown concentration will be described with reference to FIGS. 25 to 26. First, the blood clotting time reference sample of the lot B is measured using the reagent of the lot A in the reagent vessel 2, and a signal reference value $S_{Local\_2}$ for the reagent vessel 2 is set (see FIG. 25A). Subsequently, as shown in FIG. 23A, $S_{Local\_2}$ is applied to the reaction curve of the blood clotting time reference sample at three concentrations, and blood clotting times T1', T2', and T3' are calculated (FIG. 25B). Subsequently, the concentration of the standard sample and the obtained T1', T2', and T3' are plotted, whereby the standard curve for the reagent vessel 2 is created (FIG. 25C). Here, the blood clotting reaction curve of the sample with an unknown concentration is obtained as a blood clotting reaction curve (a) in FIG. 25D, the blood clotting time Tx obtained using $S_{Local\_2}$ is applied to the standard curve created in FIG. 25C, and the concentration Cx of the sample with an unknown concentration is calculated (see FIG. 25E).

That is, since the difference between the reagent vessels is corrected by setting the signal reference values intrinsic to each of the reagent vessel 1 and the reagent vessel 2, a more accurate result can be provided for the quantitative determination of the sample with an unknown concentration by creating a standard curve without performing new calibration in the reagent vessel 2.

Incidentally, when the standard curve in the PT analysis is created, there is a case where the standard curve for each facility is not created and used, but the result of the standard curve provided by the manufacturer of the reagent is obtained through a network, a bar code, or the like and used. The standard curve provided by the manufacturer of the reagent refers to a standard curve created based on the result measured using a reagent having been sufficiently tested and a sample with a known concentration, and it is not necessary to perform calibration in a facility, and therefore, the burden on the examiner and the running cost can be reduced, however, it is also considered that an error derived from a difference between devices often leads to the occurrence of an error in the measurement result. However, also in this case, an accurate measurement result can be obtained without newly creating a standard curve in a facility by setting the signal reference value according to the procedure in FIGS. 25 to 26 to reduce the difference between devices.

Third Embodiment

A third embodiment of the invention will be described with reference to the drawings.

In this embodiment, the signal reference value setting process in the first embodiment is performed by reflecting the status of degradation of the reagent and the conditions of the device (such as a change in the amount of light).

FIG. 26 is an explanatory view showing a day-to-day variation in the measurement result of the control sample in the case where the analysis item is a PT.

In the automatic analysis device, a method in which measurement using a sample with a known concentration, for example, a control sample is periodically performed, and in the case where the measurement result is outside the range of variation of the expected value determined using a specific lot and a sample, correction is performed by performing calibration is generally used. For example, as shown in FIG. 26, with respect to the accuracy control of the PT, the accuracy control is periodically performed, and the conditions of the reagent are checked. In the case where the measurement result is outside the range of variation of 3SD, calibration is performed. However, accompanying this operation, the cost of the reagent, standard sample, and consumables is increased. Therefore, by resetting the signal reference value for calculating the blood clotting time, the same effect as in the case of performing calibration is obtained even without actually measuring the standard sample. It does not matter whether the reagent to be used in this case is a lyophilized product or a liquid reagent.

Then, in the blood clotting reaction curve of the blood clotting time reference sample, the signal reference value is reset so as to match the expected value Te of the blood clotting time. However, also in this case, it is limited in a range in which the signal reference value can vary in the blood clotting reaction curve, that is, in a range in which the light intensity is more than 0% and less than 100%, that is, in a range excluding the above-mentioned base line region and plateau region, and in the case where the calculated blood clotting time is largely deviated from the allowable range, an alarm is output. In addition, it is also possible to perform the resetting of this signal reference value automatically, or to let an operator to determine whether or not the resetting of the signal reference value is performed. In this manner, the same effect as that in the case where a standard curve is created again can be obtained even if the standard sample is not measured, and thus, it can contributes to the reduction of the running cost required for the test and also a reliable result can be provided.

REFERENCE SINGS LIST 100 automatic analysis device
101 sample dispensing probe (sample dispensing mechanism)
102 sample disk
103 sample vessel
104 reaction vessel
105 sample syringe pump
106 reagent dispensing probe (reagent dispensing mechanism)
107 reagent disk
108 reagent vessel
109 reagent heating mechanism
110 reagent syringe pump
111 reaction vessel container
112 gripper
113 detection unit
114 reaction vessel placing section
115 light source
116 detection section (light sensor)
117 waste box
118 operation section
119 storage section
120 control section
120a overall control section
120b measurement control section
120c signal reference value setting control section
121 A/D converter
122 interface
123 printer

The invention claimed is:

1. An automatic analysis device, comprising:
a sample vessel placing section in which a first sample vessel containing a biological sample to be analyzed and a second sample vessel containing a blood clot time reference sample that has a known blood clot time are placed;
a reagent vessel placing section in which a plurality of reagent vessels each containing a reagent and each having a barcode attached thereto are placed;
a reaction vessel;
a sample dispensing mechanism which dispenses the biological sample or the blood clot time reference sample into the reaction vessel;
a reagent dispensing mechanism which dispenses the reagent into the reaction vessel from the reagent vessel;
a detector which detects a signal value that changes over time in accordance with a mixing reaction of the reagent and the biological sample or the blood clot time reference sample;
a barcode reader;
a control section programmed to:
control the barcode reader to read information from a barcode on a first reagent vessel of the plurality of reagent vessels,
obtain an expected blood clot time based on the information read from the barcode,
control the detector to detect first signal values from a mixture of the blood clot time reference sample and the reagent and generate a first reaction curve based on the first signal values,
determine a signal reference value based on the first reaction curve and the expected blood clot time,
store the signal reference value in association with identification information of the reagent,
control the detector to detect second signal values from a mixture of the biological sample and the reagent and generate a second reaction curve based on the second signal values,
determine whether the expected value of blood clotting time is in a predetermined range,
upon determining the blood clotting time is not in the range, issue an alarm on a display, and
determine the blood clotting time of the biological sample based on the signal reference value and the second reaction curve of the biological sample.

2. The automatic analysis device according to claim 1, wherein the one or more first signal values and the one or more second signal values indicate any one of transmitted light, an amount of scattered light, an amount of fluorescence, and a turbidity.

3. The automatic analysis device according to claim 1, wherein the control section is programmed to display a status of the signal reference value for each of a plurality of reagents, including the reagent, on the display, and display an alarm upon determining a signal reference value has not been set for any of the plurality of reagents,
wherein the status indicates at least whether a corresponding signal reference value has been set for each of the reagents.

4. The automatic analysis device according to claim 1, wherein
the control section is programmed to determine another signal reference value based on a third reaction curve generated based on controlling the detector to detect third signal values from a mixture of another blood clot time reference sample and the reagent, determine an approximate formula based on the signal reference value and the another signal reference value, and determine a third signal reference value based on the determined approximate formula, and determine the blood clotting time of the biological sample based on the third signal reference value.

5. The automatic analysis device according to claim 4, wherein the approximate formula is formed by any one method of linear approximation, polynomial approximation, logarithmic approximation, and exponential approximation.

6. A sample analysis method using an automatic analysis device which includes:

a sample vessel placing section in which a first sample vessel containing a biological sample to be analyzed and a second sample vessel containing a blood clot time reference sample that has a known blood clot time are placed;

a reagent vessel placing section in which a plurality of reagent vessels each containing a reagent and each having a barcode attached thereto are placed;

a reaction vessel;

a sample dispensing mechanism which dispenses the biological sample or the blood clot time reference sample into the reaction vessel;

a reagent dispensing mechanism which dispenses the reagent of the into the reaction vessel from the reagent vessel;

a detector which detects a signal value that changes over time in accordance with a mixing reaction of the reagent and the biological sample or the blood clot time reference sample; and a barcode reader; and a control section, the method comprising steps executed by the control section of:

controlling the barcode reader to read information from a barcode on a first reagent vessel of the plurality of reagent vessels;

obtaining an expected blood clot time based on the information read from the barcode;

controlling the detector to detect first signal values from a mixture of the blood clot time reference sample and the reagent and generate a first reaction curve based on the first signal values;

determining a signal reference value based on the first reaction curve and the expected blood clot time;

storing the signal reference value in association with identification information of the reagent; and controlling the detector to detect second signal values from a mixture of the biological sample and the reagent and generate a second reaction curve based on the second signal values;

determining whether the expected value of blood clotting time is in a predetermined range;

upon determining the blood clotting time is not in the range, issue an alarm on a display; and determining the blood clotting time of the biological sample based on the signal reference value and the second reaction curve of the biological sample.

\* \* \* \* \*